US005968809A

United States Patent [19]

[11] Patent Number: 5,968,809

[45] Date of Patent: Oct. 19, 1999

Knutzon et al.

[54] METHODS AND COMPOSITIONS FOR SYNTHESIS OF LONG CHAIN POLY-UNSATURATED FATTY ACIDS

[75] Inventors: Deborah Knutzon, Granite Bay, Calif.; Pradip Mukerji, Gahanna, Ohio; Yung-Sheng Huang, Upper Arlington, Ohio; Jennifer Thurmond, Columbus, Ohio; Sunita Chaudhary, Westerville, Ohio

[73] Assignees: Abbot Laboratories, Abbot Park, Ill.; Calgene Inc., Davis, Calif.

[21] Appl. No.: 08/834,655

[22] Filed: Apr. 11, 1997

[51] Int. Cl.[6] .............................. C12N 1/16; C07H 21/04

[52] U.S. Cl. ................. 435/254.2; 435/189; 435/254.21; 435/325; 435/410; 435/320.1; 536/23.1; 536/23.2; 536/23.7; 536/23.74; 536/24.32

[58] Field of Search ................................ 435/189, 252.3, 435/252.33, 320.1, 254.1, 254.11, 254.2, 254.21, 257.2; 536/23.1, 23.2, 23.7, 23.74, 24.32

[56] References Cited

U.S. PATENT DOCUMENTS

| | | | |
|---|---|---|---|
| 3,649,295 | 3/1972 | Bernhart | 99/57 |
| 4,058,594 | 11/1977 | Williams | 424/37 |
| 4,526,793 | 7/1985 | Ingenbleek et al. | 426/72 |
| 4,526,902 | 7/1985 | Rubin | 514/560 |
| 4,614,663 | 9/1986 | Rule | 426/601 |
| 4,670,285 | 6/1987 | Clandinin et al. | 426/602 |
| 4,843,095 | 6/1989 | Rubin | 514/558 |
| 4,920,098 | 4/1990 | Cotter et al. | 514/2 |
| 4,938,984 | 7/1990 | Traitler et al. | 426/580 |
| 5,374,657 | 12/1994 | Kyle | 514/547 |
| 5,376,541 | 12/1994 | Kawashima et al. | 435/136 |
| 5,407,957 | 4/1995 | Kyle et al. | 514/547 |
| 5,443,974 | 8/1995 | Hitz et al. | 435/172.3 |
| 5,492,938 | 2/1996 | Kyle et al. | 514/786 |
| 5,512,482 | 4/1996 | Voelker et al. | 435/320.1 |
| 5,545,553 | 8/1996 | Gotschlich | 435/252.33 |
| 5,550,156 | 8/1996 | Kyle | 514/547 |
| 5,552,306 | 9/1996 | Thomas et al. | 435/134 |
| 5,614,400 | 3/1997 | Cahoon et al. | 435/172.3 |

FOREIGN PATENT DOCUMENTS

| | | |
|---|---|---|
| 0561569 | 9/1993 | European Pat. Off. . |
| WO 93/06712 | 4/1993 | WIPO . |
| WO 94/11516 | 5/1994 | WIPO . |
| WO 94/18337 | 8/1994 | WIPO . |
| WO 96/10086 | 4/1996 | WIPO . |
| WO 96/21022 | 7/1996 | WIPO . |
| WO 97/30582 | 8/1997 | WIPO . |

OTHER PUBLICATIONS

Ackman, "Problems in fish oils and concentrates," Canadian Institute of Fisheries Technology, Technical University of Nova Scotia, 189–204.

Bajpai and Bajpai, "Arachidonic Acid Production by Microorganisms," Biotechnology and Applied Biochemistry 15:1–10 (1992).

Gurr, "Alpha or gamma: what's a double bond position between friends? 1. Gamma–linolenic acid," Lipid Technology (Mar. 1995).

Hodgson, "Advances in vector systems for gene therapy," Ex. Opin. Ther. Patents 5(5):459–468 (1995).

Horrobin, "Medical roles of metabolites of precursor EFA," INFORM 6(4):428–434 (Apr. 1995).

Murata et al., "Biosynthesis of gamma–Linolenic Acid in the Cyanobacterium *Spiruline platensis,*" In: gamma–Linolenic Acid Metabolism and Its Roles in Nutrition and Medicine (Huang and Mills, eds.), pp. 22–32, Access Press, Champain, IL.

Ratledge, "Single cell oils–have they a biotechnological future?" MB Tech. 11 (Jul. 1995).

Reddy and Thomas, "Expression of a cyanobacterial $\Delta^6$—desaturase gene results in gamma–linolenic acid production in transgenic plants," Nature Biotechnology 14:639–642 (May 1996).

Ward, "Microbial production of long–chain PUFAs," INFORM 6(6):683–688 (Jun. 1995).

"Closer to Mother's Milk, " the Gist 61:8–9 (Spring 1995).

"Exciting prospects for stearidonic acid seed oils," Lipid Technology (Nov. 1996).

Covello, P. et al., "Functional Expression of teh Extraplastidial Arabidopsis Thaliana Oleate Desaturase Gene (FAD2) in Saccharomyces Cerevisiae", Plant Physiology, vol. 111, No. 1, pp.223–226, (1996).

Yoshino, R., et al., "Development cDNA in Dictyostelium Discoideum", EMBL Database, (1997).

*Primary Examiner*—Ponnathapura Achutamurthy
*Assistant Examiner*—Nashaat T. Nashed
*Attorney, Agent, or Firm*—Limbach & Limbach L.L.P.

[57] ABSTRACT

The present invention relates to fatty acid desaturases able to catalyze the conversion of oleic acid to linoleic acid, linoleic acid to gamma-linolenic acid, or of alpha-linolenic acid to stearidonic acid. Nucleic acid sequences encoding desaturases, nucleic acid sequences which hybridize thereto, DNA constructs comprising a desaturase gene, and recombinant host microorganism or animal expressing increased levels of a desaturase are described. Methods for desaturating a fatty acid and for producing a desaturated fatty acid by expressing increased levels of a desaturase are disclosed. Fatty acids, and oils containing them, which have been desaturated by a desaturase produced by recombinant host microorganisms or animals are provided. Pharmaceutical compositions, infant formulas or dietary supplements containing fatty acids which have been desaturated by a desaturase produced by a recombinant host microorganism or animal also are described.

30 Claims, 16 Drawing Sheets

```
                                                                          60
                                                                           *
CGACACTCCT TCCTTCTTCT CACCCGTCCT AGTCCCCTTC AACCCCCCTC TTTGACAAAG

ACAACAAACC ATG GCT GCT GCT CCC AGT GTG AGG ACG TTT ACT CGG GCC GAG
           Met Ala Ala Ala Pro Ser Val Arg Thr Phe Thr Arg Ala Glu

        120
         *
GTT TTG AAT GCC GAG GCT CTG AAT GAG GGC AAG AAG GAT GCC GAG GCA
Val Leu Asn Ala Glu Ala Leu Asn Glu Gly Lys Lys Asp Ala Glu Ala

                            180
                             *
CCC TTC TTG ATG ATC ATC GAC AAC AAG GTG TAC GAT GTC CGC GAG TTC
Pro Phe Leu Met Ile Ile Asp Asn Lys Val Tyr Asp Val Arg Glu Phe

                                            240
                                             *
GTC CCT GAT CAT CCC GGT GGA AGT GTG ATT CTC ACG CAC GTT GGC AAG
Val Pro Asp His Pro Gly Gly Ser Val Ile Leu Thr His Val Gly Lys

                                                            300
                                                             *
GAC GGC ACT GAC GTC TTT GAC ACT TTT CAC CCC GAG GCT GCT TGG GAG
Asp Gly Thr Asp Val Phe Asp Thr Phe His Pro Glu Ala Ala Trp Glu

ACT CTT GCC AAC TTT TAC GTT GGT GAT ATT GAC GAG AGC GAC CGC GAT
Thr Leu Ala Asn Phe Tyr Val Gly Asp Ile Asp Glu Ser Asp Arg Asp

        360
         *
ATC AAG AAT GAT GAC TTT GCG GCC GAG GTC CGC AAG CTG CGT ACC TTG
Ile Lys Asn Asp Asp Phe Ala Ala Glu Val Arg Lys Leu Arg Thr Leu
```

FIG. 3A

```
                                    420
                                     *
TTC CAG TCT CTT GGT TAC TAC GAT TCT TCC AAG GCA TAC TAC GCC TTC
Phe Gln Ser Leu Gly Tyr Tyr Asp Ser Ser Lys Ala Tyr Tyr Ala Phe
                                                480
                                                 *
AAG GTC TCG TTC AAC CTC TGC ATC TGG GGT TTG TCG ACG GTC ATT GTG
Lys Val Ser Phe Asn Leu Cys Ile Trp Gly Leu Ser Thr Val Ile Val
                                                            540
                                                             *
GCC AAG TGG GGC CAG ACC TCG ACC CTC GCC AAC GTG CTC TCG GCT GCG
Ala Lys Trp Gly Gln Thr Ser Thr Leu Ala Asn Val Leu Ser Ala Ala

CTT TTG GGT CTG TTC TGG CAG CAG TGC GGA TGG TTG GCT CAC GAC TTT
Leu Leu Gly Leu Phe Trp Gln Gln Cys Gly Trp Leu Ala His Asp Phe
        600
         *
TTG CAT CAC CAG GTC TTC CAG GAC CGT TTC TGG GGT GAT CTT TTC GGC
Leu His His Gln Val Phe Gln Asp Arg Phe Trp Gly Asp Leu Phe Gly
                            660
                             *
GCC TTC TTG GGA GGT GTC TGC CAG GGC TTC TCG TCC TCG TGG TGG AAG
Ala Phe Leu Gly Gly Val Cys Gln Gly Phe Ser Ser Ser Trp Trp Lys
                                            720
                                             *
GAC AAG CAC AAC ACT CAC CAC GCC GCC CCC AAC GTC CAC GGC GAG GAT
Asp Lys His Asn Thr His His Ala Ala Pro Asn Val His Gly Glu Asp
                                                            780
                                                             *
```

FIG. 3B

```
CCC GAC ATT GAC ACC CAC CCT CTG TTG ACC TGG AGT GAG CAT GCG TTG
Pro Asp Ile Asp Thr His Pro Leu Leu Thr Trp Ser Glu His Ala Leu

GAG ATG TTC TCG GAT GTC CCA GAT GAG GAG CTG ACC CGC ATG TGG TCG
Glu Met Phe Ser Asp Val Pro Asp Glu Glu Leu Thr Arg Met Trp Ser
        840
         *
CGT TTC ATG GTC CTG AAC CAG ACC TGG TTT TAC TTC CCC ATT CTC TCG
Arg Phe Met Val Leu Asn Gln Thr Trp Phe Tyr Phe Pro Ile Leu Ser
                        900
                         *
TTT GCC CGT CTC TCC TGG TGC CTC CAG TCC ATT CTC TTT GTG CTG CCT
Phe Ala Arg Leu Ser Trp Cys Leu Gln Ser Ile Leu Phe Val Leu Pro
                                        960
                                         *
AAC GGT CAG GCC CAC AAG CCC TCG GGC GCG CGT GTG CCC ATC TCG TTG
Asn Gly Gln Ala His Lys Pro Ser Gly Ala Arg Val Pro Ile Ser Leu
                                                        1020
                                                          *
GTC GAG CAG CTG TCG CTT GCG ATG CAC TGG ACC TGG TAC CTC GCC ACC
Val Glu Gln Leu Ser Leu Ala Met His Trp Thr Trp Tyr Leu Ala Thr

ATG TTC CTG TTC ATC AAG GAT CCC GTC AAC ATG CTG GTG TAC TTT TTG
Met Phe Leu Phe Ile Lys Asp Pro Val Asn Met Leu Val Tyr Phe Leu
       1080
         *
GTG TCG CAG GCG GTG TGC GGA AAC TTG TTG GCG ATC GTG TTC TCG CTC
Val Ser Gln Ala Val Cys Gly Asn Leu Leu Ala Ile Val Phe Ser Leu
```

FIG. 3C

```
                              1140
                                 *
AAC CAC AAC GGT ATG CCT GTG ATC TCG AAG GAG GAG GCG GTC GAT ATG
Asn His Asn Gly Met Pro Val Ile Ser Lys Glu Glu Ala Val Asp Met
                                            1200
                                               *
GAT TTC TTC ACG AAG CAG ATC ATC ACG GGT CGT GAT GTC CAC CCG GGT
Asp Phe Phe Thr Lys Gln Ile Ile Thr Gly Arg Asp Val His Pro Gly
                                                        1260
                                                           *
CTA TTT GCC AAC TGG TTC ACG GGT GGA TTG AAC TAT CAG ATC GAG CAC
Leu Phe Ala Asn Trp Phe Thr Gly Gly Leu Asn Tyr Gln Ile Glu His

CAC TTG TTC CCT TCG ATG CCT CGC CAC AAC TTT TCA AAG ATC CAG CCT
His Leu Phe Pro Ser Met Pro Arg His Asn Phe Ser Lys Ile Gln Pro
        1320
           *
GCT GTC GAG ACC CTG TGC AAA AAG TAC AAT GTC CGA TAC CAC ACC ACC
Ala Val Glu Thr Leu Cys Lys Lys Tyr Asn Val Arg Tyr His Thr Thr
                            1380
                               *
GGT ATG ATC GAG GGA ACT GCA GAG GTC TTT AGC CGT CTG AAC GAG GTC
Gly Met Ile Glu Gly Thr Ala Glu Val Phe Ser Arg Leu Asn Glu Val
                                            1440
                                               *
TCC AAG GCT GCC TCC AAG ATG GGT AAG GCG CAG TAAAAAAAA AAACAAGGAC
Ser Lys Ala Ala Ser Lys Met Gly Lys Ala Gln
```

FIG. 3D

```
                                       1500
                                          *
GTTTTTTTTC GCCAGTGCCT GTGCCTGTGC CTGCTTCCCT TGTCAAGTCG AGCGTTTCTG
                                       1560
                                          *
GAAAGGATCG TTCAGTGCAG TATCATCATT CTCCTTTTAC CCCCCGCTCA TATCTCATTC

ATTTCTCTTA TTAAACAACT TGTTCCCCCC TTCACCG
```

FIG. 3E

```
Ma524     EVRKLRTLFQSLGYYDSSKAYYAFKVSFNLCIWGLSTVIVAKWGQTSTLANVLSAALLGL 90
ATTS4723  ---------------------VTLY-TLAFVAAMSLGVLYGVLACPSVXPHQIAAGLLGL 38
12-5      ------------------------------------GVLYGVLACTSVFAHQIAAALLGL 24
T42806    -----GXX---------------------------------------------------- 4
W28140    ------------------------------------------------------------ 1
R05219    ------------------------------C----------------------------- 2
W53753    ------------------------------------------------------------ 1

Ma524     FWQQCGWLAHDFLHHQVFQDRFWGDL-FGAFLGGVC-QGFSSSWWKDKHNTHHAAPNVHGE 119
ATTS4723  LWIQSAYIGXDSGHYVIMSNKSNNX-FAQLLSGNCLTGI IAWWKWTHNAHHLACNSLDY 97
12-5      LWIQSAYIGHDSGHYVIMSNKSYNR-FAQLLSGNCLTGISIAWWKWTHNAHHLACNSLDY 83
T42806    ------------------------------------------------------------ 4
W28140    ------------------------------------------------------------ 1
R05219    ------------------------------------------------------------ 2
W53753    ------------------------------------------------------------ 1

Ma524     DPDIDTHPLLTWSEHALEMFSDVPDEELTRMWS-----RFMVLNQTWFYFPILSFARLSW 174
ATTS4723  GPNLQHIP                                                     105
12-5      DPDLQHIPVFAVSTK---FFSSLTSRFYDRKLTFGPVARFLVSYQHFTYYPVMCFGRINL 140
T42806    ------------------------------------------------------------ 4
W28140    ------------------------------------------------------------ 1
R05219    ------------------------------------------------------------ 2
W53753    ------------------------------------------------------------ 1
```

FIG. 4A

```
Ma524     CLQSILFVLPNGQAHKPSGARVPISLVEQLSLAM-----HWTWYLATMFLFIKDPVNMLV 229
ATTS4723                                         W W                   105
12-5      FIQTFLLLFSKRE--------VPDRALNFAGILV-----FWTWF--PLLVSCLPNWPERF 185
T42806    ------------------------------NFAGILV-----FFTVF--PLLVSCLPNWPERF 29
W28140    ------------------------------PATEVGGLAWMIT-Y-RFFLTYVPLLGLKAFLG 33
R05219    ----------------------------------------F-S------------------- 2
W53753    -----------RHEAARGGTRLAYMLVCMQWTDL--LWAAS Y RFFLSYSPFYGATGTLL 48

Ma524     YFLVSQAVCGNLLAIVFSLNHNGMPVISKEEAVDMDFFTKQIITGRDVHPGLFANWFTGG 289
ATTS4723                                                               105
12-5      FFVFTSFTVTALQHIQFTLNHFAADVYV-GPPTGSDWFEKQAAGTIDISCRSYMDWFFGG 244
T42806    XFVFTGFTVTALQHIQFTLNHFAADVYV-GPPTGSDWFEKQAAGTIDISCRSYMDWFFGG 88
W28140    LFFIVRFLESNWFVWVTQMNH---IPMHIDHDRNMDWVSTQLQATCNVHKSAFNIDWFSGH 90
R05219    ------------------------------------------SPKSSPTRNMTPSPFIDWLWGG 23
W53753    LFVAVRVLESHWFVWITQMNH---IPKEIGHEKHRDWASSQLAATCNVEPSLF DWFSGH 105

Ma524     LNYQIEHHLFPSMPRHNFSKIQPAVETLCKKYNVRYHTTGMIEGTAEVESRLNEVSKAAS 349
ATTS4723                                                               105
12-5      LQFQLEHH                                                     252
T42806    LQFQLEHHLFPRLPRCHLRKVSPVGQRGFQRKXNLSX                        125
W28140    LNFQIEHHLFPTMPRHNYHXVAPLVQSLCAKHGIEYQSKPL                    131
R05219    LNYQIEHHLFPTMPRCNLNRCMKYVKEWCAENNLPYLVDDYFVGYNLNLQQLKNMAELVQ 83
W53753    LNFQIEHHLFPTMPRHNYRXVAPLVKAFCAKHGLHYEV                       143

Ma524     KMGKAQ                                                       355
ATTS4723                                                               105
12-5                                                                   252
T42806                                                                 125
W28140                                                                 131
R05219    --AKAA                                                       87
W53753                                                                 148
```

FIG. 4B

```
                                                                   60
                                                                    *
GTCCCCTGTC GCTGTCGGCA CACCCCATCC TCCCTCGCTC CCTCTGCGTT TGTCCTTGGC
                                                                  120
                                                                    *
CCACCGTCTC TCCTCCACCC TCCGAGACGA CTGCAACTGT AATCAGGAAC CGACAAATAC
                                                                    180
                                                                      *
ACGATTTCTT TTTACTCAGC ACCAACTCAA AATCCTCAAC CGCAACCCTT TTTCAGG ATG
                                                                Met
GCA CCT CCC AAC ACT ATC GAT GCC GGT TTG ACC CAG CGT CAT ATC AGC
Ala Pro Pro Asn Thr Ile Asp Ala Gly Leu Thr Gln Arg His Ile Ser
             240
               *
ACC TCG GCC CCA AAC TCG GCC AAG CCT GCC TTC GAG CGC AAC TAC CAG
Thr Ser Ala Pro Asn Ser Ala Lys Pro Ala Phe Glu Arg Asn Tyr Gln
                                 300
                                   *
CTC CCC GAG TTC ACC ATC AAG GAG ATC CGA GAG TGC ATC CCT GCC CAC
Leu Pro Glu Phe Thr Ile Lys Glu Ile Arg Glu Cys Ile Pro Ala His
                                                 360
                                                   *
TGC TTT GAG CGC TCC GGT CTC CGT GGT CTC TGC CAC GTT GCC ATC GAT
Cys Phe Glu Arg Ser Gly Leu Arg Gly Leu Cys His Val Ala Ile Asp
                                                             420
                                                               *
CTG ACT TGG GCG TCG CTC TTG TTC CTG GCT GCG ACC CAG ATC GAC AAG
Leu Thr Trp Ala Ser Leu Leu Phe Leu Ala Ala Thr Gln Ile Asp Lys

TTT GAG AAT CCC TTG ATC CGC TAT TTG GCC TGG CCT GTT TAC TGG ATC
Phe Glu Asn Pro Leu Ile Arg Tyr Leu Ala Trp Pro Val Tyr Trp Ile
```

FIG. 5A

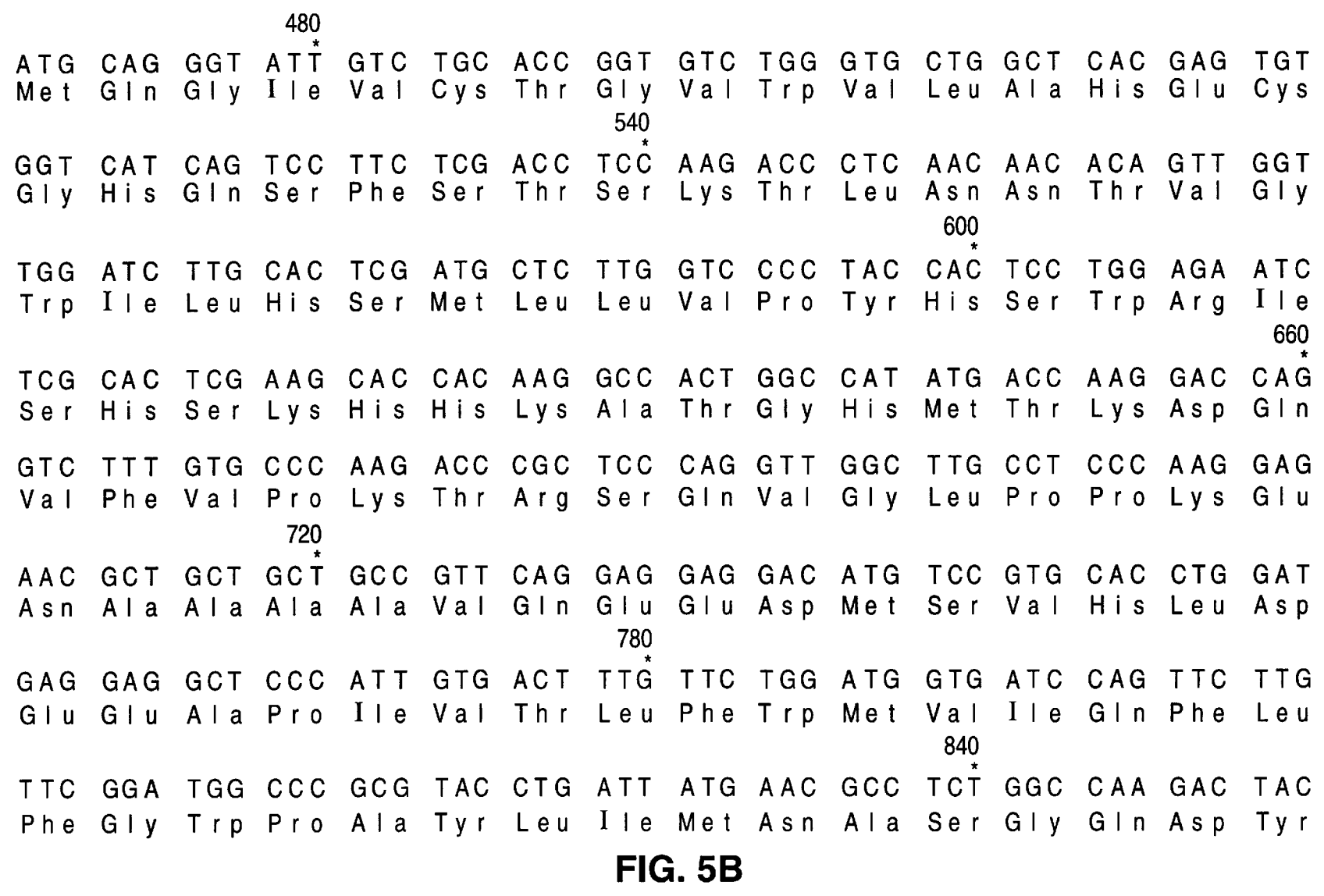

```
                        480
                          *
ATG CAG GGT ATT GTC TGC ACC GGT GTC TGG GTG CTG GCT CAC GAG TGT
Met Gln Gly Ile Val Cys Thr Gly Val Trp Val Leu Ala His Glu Cys
                                    540
                                      *
GGT CAT CAG TCC TTC TCG ACC TCC AAG ACC CTC AAC AAC ACA GTT GGT
Gly His Gln Ser Phe Ser Thr Ser Lys Thr Leu Asn Asn Thr Val Gly
                                                600
                                                  *
TGG ATC TTG CAC TCG ATG CTC TTG GTC CCC TAC CAC TCC TGG AGA ATC
Trp Ile Leu His Ser Met Leu Leu Val Pro Tyr His Ser Trp Arg Ile
                                                            660
                                                              *
TCG CAC TCG AAG CAC CAC AAG GCC ACT GGC CAT ATG ACC AAG GAC CAG
Ser His Ser Lys His His Lys Ala Thr Gly His Met Thr Lys Asp Gln

GTC TTT GTG CCC AAG ACC CGC TCC CAG GTT GGC TTG CCT CCC AAG GAG
Val Phe Val Pro Lys Thr Arg Ser Gln Val Gly Leu Pro Pro Lys Glu
                720
                  *
AAC GCT GCT GCT GCC GTT CAG GAG GAG GAC ATG TCC GTG CAC CTG GAT
Asn Ala Ala Ala Ala Val Gln Glu Glu Asp Met Ser Val His Leu Asp
                                    780
                                      *
GAG GAG GCT CCC ATT GTG ACT TTG TTC TGG ATG GTG ATC CAG TTC TTG
Glu Glu Ala Pro Ile Val Thr Leu Phe Trp Met Val Ile Gln Phe Leu
                                                840
                                                  *
TTC GGA TGG CCC GCG TAC CTG ATT ATG AAC GCC TCT GGC CAA GAC TAC
Phe Gly Trp Pro Ala Tyr Leu Ile Met Asn Ala Ser Gly Gln Asp Tyr
```

FIG. 5B

```
                                                                 900
                                                                   *
GGC CGC TGG ACC TCG CAC TTC CAC ACG TAC TCG CCC ATC TTT GAG CCC
Gly Arg Trp Thr Ser His Phe his Thr Tyr Ser Pro Ile Phe Glu Pro

CGC AAC TTT TTC GAC ATT ATT ATC TCG GAC CTC GGT GTG TTG GCT GCC
Arg Asn Phe Phe Asp Ile Ile Ile Ser Asp Leu Gly Val Leu Ala Ala
             960
               *
CTC GGT GCC CTG ATC TAT GCC TCC ATG CAG TTG TCG CTC TTG ACC GTC
Leu Gly Ala Leu Ile Tyr Ala Ser Met Gln Leu Ser Leu Leu Thr Val
                             1020
                               *
ACC AAG TAC TAT ATT GTC CCC TAC CTC TTT GTC AAC TTT TGG TTG GTC
Thr Lys Tyr Tyr Ile Val Pro Tyr Leu Phe Val Asn Phe Trp Lru Val
                                         1080
                                           *
CTG ATC ACC TTC TTG CAG CAC ACC GAT CCC AAG CTG CCC CAT TAC CGC
Leu Ile Thr Phe Leu Gln His Thr Asp Pro Lys Leu Pro His Tyr Arg
                                                            1140
                                                               *
GAG GGT GCC TGG AAT TTC CAG CGT GGA GCT CTT TGC ACC GTT GAC CGC
Glu Gly Ala Trp Asn Phe Gln Arg Gly Ala Leu Cys Thr Val Asp Arg

TCG TTT GGC AAG TTC TTG GAC CAT ATG TTC CAC GGC ATT GTC CAC ACC
Ser Phe Gly Lys Phe Leu Asp His Met Phe His Gly Ile Val His Thr
            1200
               *
CAT GTG GCC CAT CAC TTG TTC TCG CAA ATG CCG TTC TAC CAT GCT GAG
His Val Ala His His Leu Phe Ser Gln Met Pro Phe Tyr His Ala Glu
```

FIG. 5C

```
                                                  1260
                                                     *
GAA GCT ACC TAT CAT CTC AAG AAA CTG CTG GGA GAG TAC TAT GTG TAC
Glu Ala Thr Tyr His Leu Lys Lys Leu Leu Gly Glu Tyr Tyr Val Tyr

                                                      1320
                                                         *
GAC CCA TCC CCG ATC GTG GTT GCG GTC TGG AGG TCG TTC CGT GAG TGC
Asp Pro Ser Pro Ile Val Val Ala Val Trp Arg Ser Phe Arg Glu Cys

                                                                1380
                                                                   *
CGA TTC GTG GAG GAT CAG GGA GAC GTG GTC TTT TTC AAG AAG TAAAAA
Arg Phe Val Glu Asp Gln Gly Asp Val Val Phe Phe Lys Lys

                                                                1440
                                                                   *
AAAAGACAAT GGACCACACA CAACCTTGTC TCTACAGACC TACGTATCAT GTAGCCATAC

CACTTCATAA AAGAACATGA GCTCTAGAGG CGTGTCATTC GCGCCTCC
```

FIG. 5D

METHODS AND COMPOSITIONS FOR SYNTHESIS OF LONG CHAIN POLY-UNSATURATED FATTY ACIDS

INTRODUCTION

1. Field of the Invention

This invention relates to modulating levels of enzymes and/or enzyme components relating to production of long chain poly-unsaturated fatty acids (PUFAs) in a microorganism or animal. The invention is exemplified by the production of gamma-linolenic acid and stearidonic acid in yeast.

2. Background

Two main families of poly-unsaturated fatty acids (PUFAs) are the ω3 fatty acids, exemplified by eicosapentaenoic acid (EPA), and the ω6 fatty acids, exemplified by arachidonic acid (ARA). PUFAs are important components of the plasma membrane of the cell, where they may be found in such forms as phospholipids and triglycerides. PUFAs are necessary for proper development, particularly in the developing infant brain, and for tissue formation and repair. PUFAs also serve as precursors to other molecules of importance in human beings and animals, including the prostacyclins, eicosanoids, leukotrienes and prostaglandins. Four major long chain PUFAs of importance include docosahexaenoic acid (DHA) and EPA, which are primarily found in different types of fish oil, gamma-linolenic acid (GLA), which is found in the seeds of a number of plants, including evening primrose (*Oenothera biennis*), borage (*Borago officinalis*) and black currants (*Ribes nigrum*), and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland. GLA, ARA, EPA and SDA are themselves, or are dietary precursors to, important long chain fatty acids involved in prostaglandin synthesis, in treatment of heart disease, and in development of brain tissue.

Several disorders respond to treatment with fatty acids. Supplementation with PUFAs has been shown to reduce the rate of restenosis after angioplasty. Fish oil supplements have been shown to improve symptoms of inflammation and rheumatoid arthritis, and PUFAs have been suggested as treatments for asthma and psoriasis. Evidence indicates that PUFAs may be involved in calcium metabolism, suggesting that PUFAs may be usefull in the treatment or prevention of osteoporosis and of kidney or urinary tract stones.

PUFAs can be used in the treatment of cancer. Malignant cells have been shown to have altered fatty acid compositions; addition of fatty acids has been shown to slow their growth and cause cell death, and to increase their susceptibility to chemotherapeutic agents. GLA has been shown to cause reexpression on cancer cells of the E-cadherin cellular adhesion molecules, loss of which is associated with aggressive metastasis. Clinical testing of intravenous administration of the water soluble lithium salt of GLA to pancreatic cancer patients produced statistically significant increases in their survival. PUFA supplementation may also be useful for treating cachexia associated with cancer.

PUFAs also can be used to treat diabetes (U.S. Pat. No. 4,826,877; Horrobin et al., Am. J. Clin. Nutr. Vol. 57 (Suppl.), 732S–737S). Altered fatty acid metabolism and composition has been demonstrated in diabetic animals. These alterations have been suggested to be involved in some of the long-term complications resulting from diabetes, including retinopathy, neuropathy, nephropathy and reproductive system damage. Primrose oil, which contains GLA, has been shown to prevent and reverse diabetic nerve damage.

Essential fatty acid deficiency has been suggested as being involved in eczema, and studies have shown beneficial effects on eczema from treatment with GLA. GLA has also been shown to reduce increases in blood pressure associated with stress, and to improve performance on arithmetic tests. GLA and DGLA have been shown to inhibit platelet aggregation, cause vasodilation, lower cholesterol levels and inhibit proliferation of vessel wall smooth muscle and fibrous tissue (Brenner et al, Adv. Exp. Med. Biol. Vol. 83, p. 85–101, 1976). Administration of GLA or DGLA, alone or in combination with EPA, has been shown to reduce or prevent gastrointestinal bleeding and other side effects caused by non-steroidal anti-inflammatory drugs (U.S. Pat. No. 4,666,701). GLA and DGLA have also been shown to prevent or treat endometriosis and premenstrual syndrome (U.S. Pat. No. 4,758,592) and to treat myalgic encephalomyelitis and chronic fatigue after viral infections (U.S. Pat. No. 5,116,871).

For DHA, a number of sources exist for commercial production including a variety of marine organisms, oils obtained from cold water marine fish, and egg yolk fractions. For ARA, microorganisms including the genera Mortierella, Entomophthora, Phytium and Porphyridium can be used for commercial production. Commercial sources of SDA include the genera Trichodesma and Echium. Commercial sources of GLA include evening primrose, black currants and borage. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFA. Natural sources also are subject to uncontrollable fluctuations in availability. Fish stocks may undergo natural variation or may be depleted by overfishing. Fish oils have unpleasant tastes and odors, which may be impossible to economically separate from the desired product, and can render such products unacceptable as food supplements. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large scale fermentation of organisms such as Mortierella is also expensive. Natural animal tissues contain low amounts of ARA and are difficult to process. Microorganisms such as Porphyridium and Mortierella are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Unpleasant tastes and odors of the supplements can make such regimens undesirable, and may inhibit compliance by the patient. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603).

A number of enzymes are involved in PUFA biosynthesis. Linoleic acid (LA, 18:2 $\Delta^{9,12}$) is produced from oleic acid (18:1 $\Delta^{9}$) by a Δ12-desaturase. GLA (18:3 $\Delta^{6,9\ 12}$) is produced from linoleic acid (LA, 18:2 $\Delta^{9,12}$) by a Δ6-desaturase. ARA (20:4 $\Delta^{5,8,11,14}$) production from dihomo-gamma-linolenic acid (DGLA, 20:3 $\Delta^{8,11,14}$) is catalyzed by a Δ5-desaturase. However, animals cannot desaturate beyond the $\Delta^{9}$ position and therefore cannot convert oleic acid (18:1 $\Delta^{9}$) into linoleic acid (18:2 $\Delta^{9,12}$). Likewise, α-linolenic acid (ALA, 18:3 $\Delta^{9,12,15}$) cannot be synthesized by mammals. Other eukaryotes, including fungi and plants, have enzymes which desaturate at positions $\Delta^{12}$ and $\Delta^{15}$. The major poly-unsaturated fatty acids of animals therefore are either derived from diet and/or from desaturation and elongation of linoleic acid (18:2 $\Delta^{9,12}$) or -linolenic acid (18:3 $\Delta^{9,12,15}$). Therefore it is of interest to obtain genetic material involved in PUFA biosynthesis from species that naturally produce these fatty acids and to express the isolated material in a microbial or animal system which can be manipulated to provide production of commercial quantities of one or more PUFAs. Thus there is a need for fatty acid desaturases, genes encoding them, and recombinant methods of producing them. A need further exists for oils containing higher relative proportions of and/or enriched in specific PUFAs. A need also exists for reliable economical methods of producing specific PUFAs.

Relevant Literature

Production of gamma-linolenic acid by a Δ6-desaturase is described in U.S. Pat. No. 5,552,306. Production of 8, 11-eicosadienoic acid using *Mortierella alpina* is disclosed in U.S. Pat. No. 5,376,541. Production of docosahexaenoic acid by dinoflagellates is described in U.S. Pat. No. 5,407, 957. Cloning of a Δ6-palmitoyl-acyl carrier protein desaturase is described in PCT publication WO 96/13591 and U.S. Pat. No. 5,614,400. Cloning of a Δ6-desaturase from borage is described in PCT publication WO 96/21022. Cloning of Δ9-desaturases is described in the published patent applications PCT WO 91/13972,EP0 550 162A1, EP0 561 569A2, EP0 644 263A2, and EP0 736 598A1, and in U.S. Pat. No. 5,057,419. Cloning of Δ12-desaturases from various organisms is described in PCT publication WO 94/11516 and U.S. Pat. No. 5,443,974. Cloning of Δ15-desaturases from various organisms is described in PCT publication WO 93/11245. All publications and U.S. patents or applications referred to herein are hereby incorporated in their entirety by reference.

SUMMARY OF THE INVENTION

Novel compositions and methods are provided for preparation of poly-unsaturated long chain fatty acids. The compositions include nucleic acid encoding a Δ6- and Δ12-desaturase and/or polypeptides having Δ6- and/or Δ12-desaturase activity, the polypeptides, and probes isolating and detecting the same. The methods involve growing a host microorganism or animal expressing an introduced gene or genes encoding at least one desaturase, particularly a Δ6-, Δ9-, Δ12- or Δ15-desaturase. The methods also involve the use of antisense constructs or gene disruptions to decrease or eliminate the expression level of undesired desaturases. Regulation of expression of the desaturase polypeptide(s) provides for a relative increase in desired desaturated PUFAs as a result of altered concentrations of enzymes and substrates involved in PUFA biosynthesis. The invention finds use, for example, in the large scale production of GLA, DGLA, ARA, EPA, DHA and SDA.

In a preferred embodiment of the invention, an isolated nucleic acid comprising: a nucleotide sequence depicted in FIGS. 3A–E (SEQ ID NO: 1) or FIGS. 5A–D (SEQ ID NO: 3), a polypeptide encoded by a nucleotide sequence according FIGS. 3A–E (SEQ ID NO: 1) or FIGS. 5A–D (SEQ ID NO: 3), and a purified or isolated polypeptide comprising an amino acid sequence depicted in FIGS. 3A–E (SEQ ID NO: 2) or FIGS. 5A–D (SEQ ID NO: 4). In another embodiment of the invention, provided is an isolated nucleic acid encoding a polypeptide having an amino acid sequence depicted in FIGS. 3A–E (SEQ ID NO: 2) or FIGS. 5A–D (SEQ ID NO: 4). Also provided is an isolated nucleic acid comprising a nucleotide sequence which encodes a polypeptide which desaturates a fatty acid molecule at carbon 6 or 12, wherein said nucleotide sequence has an average A/T content of less than about 60%. In a preferred embodiment, the isolated nucleic acid is derived from a fungus, such as a fungus of the genus Mortierella. More preferred is a fungus of the species *Mortierella alpina.*

In another preferred embodiment of the invention, an isolated nucleic acid is provided wherein the nucleotide sequence of the nucleic acid is depicted in FIGS. 3A–E (SEQ ID NO: 1) or FIGS. 5A–D (SEQ ID NO: 3). The invention also provides an isolated or purified polypeptide which desaturates a fatty acid molecule at carbon 6 or 12, wherein the polypeptide is a eukaryotic polypeptide or is derived from a eukaryotic polypeptide, where a preferred eukaryotic polypeptide is derived from a fungus.

The present invention further includes a nucleic acid sequence which hybridizes to FIGS. 3A–E (SEQ ID NO: 1) or FIGS. 5A–D (SEQ ID NO: 3). Preferred is an isolated nucleic acid having a nucleotide sequence with at least about 50% homology to FIGS. 3A–E (SEQ ID NO: 1) or FIGS. 5A–D (SEQ ID NO: 3). The invention also includes an isolated nucleic acid having a nucleotide sequence with at least about 50% homology to FIGS. 3A–E (SEQ ID NO: 1) or FIGS. 5A–D (SEQ ID NO: 3). In a preferred embodiment, the nucleic acid of the invention includes a nucleotide sequence which encodes an amino acid sequence depicted in FIGS. 3A–D (SEQ ID NO: 2) which is selected from the group consisting of amino acid residues 50–53, 39–43, 172–176, 204–213, and 390–402.

Also provided by the present invention is a nucleic acid construct comprising a nucleotide sequence depicted in a FIGS. 3A–E (SEQ ID NO: 1) or FIGS. 5A–D (SEQ ID NO: 3) linked to a heterologous nucleic acid. In another embodiment, a nucleic acid construct is provided which comprises a nucleotide sequence depicted in a FIGS. 3A–E (SEQ ID NO: 1) or FIGS. 5A–D (SEQ ID NO: 3) operably associated with an expression control sequence functional in a host cell. The host cell is either eukaryotic or prokaryotic. Preferred eukaryotic host cells are those selected from the group consisting of a mammalian cell, an insect cell, a fungal cell, and an algae cell. Preferred mammalian cells include an avian cell, a preferred fungal cell includes a yeast cell, and a preferred algae cell is a marine algae cell. Preferred prokaryotic cells include those selected from the group consisting of a bacteria, a cyanobacteria, cells which contain a bacteriophage, and/or a virus. The DNA sequence of the recombinant host cell preferably contains a promoter which is functional in the host cell, which promoter is preferably inducible. In a more preferred embodiment, the microbial cell is a fungal cell of the genus Mortierella, with a more preferred fungus is of the species *Mortierella alpina*.

In addition, the present invention provides a nucleic acid construct comprising a nucleotide sequence which encodes a polypeptide comprising an amino acid sequence which corresponds to or is complementary to an amino acid sequence depicted in FIGS. 3A–E (SEQ ID NO: 2) or FIGS. 5A–D (SEQ ID NO: 4), wherein the nucleic acid is operably associated with an expression control sequence functional in a microbial cell, wherein the nucleotide sequence encodes a functionally active polypeptide which desaturates a fatty acid molecule at carbon 5 or carbon 11 from the carboxyl end of a fatty acid molecule. Another embodiment of the present invention is a nucleic acid construct comprising a nucleotide sequence which encodes a functionally active Δ6-desaturase having an amino acid sequence which corresponds to or is complementary to all of or a portion of an amino acid sequence depicted in a FIGS. 3A–E (SEQ ID NO: 2), wherein the nucleotide sequence is operably associated with a transcription control sequence functional in a host cell.

Yet another embodiment of the present invention is a nucleic acid construct comprising a nucleotide sequence which encodes a functionally active Δ12-desaturase having an amino acid sequence which corresponds to or is complementary to all of or a portion of an amino acid sequence depicted in a FIGS. 5A–D (SEQ ID NO: 4), wherein the nucleotide sequence is operably associated with a transcription control sequence functional in a host cell. The host cell, is either a eukaryotic or prokaryotic host cell. Preferred eukaryotic host cells are those selected from the group consisting of a mammalian cell, an insect cell, a fungal cell, and an algae cell. Preferred mammalian cells include an avian cell, a preferred fungal cell includes a yeast cell, and a preferred algae cell is a marine algae cell. Preferred prokaryotic cells include those selected from the group consisting of a bacteria, a cyanobacteria, cells which contain a bacteriophage, and/or a virus. The DNA sequence of the recombinant host cell preferably contains a promoter which is functional in the host cell and which preferably is inducible. A preferred recombinant host cell is a microbial cell such as a yeast cell, such as a Saccharomyces cell.

The present invention also provides a recombinant microbial cell comprising at least one copy of a nucleic acid which encodes a functionally active *Mortierella alpina* fatty acid desaturase having an amino acid sequence as depicted in FIGS. 3A–E (SEQ ID NO: 2), wherein the cell or a parent of the cell was transformed with a vector comprising said DNA sequence, and wherein the DNA sequence is operably associated with an expression control sequence. In another preferred embodiment, the microbial cell according to the invention includes an expression control sequence which is endogenous to the microbial cell.

Also provided by the present invention is a method for production of GLA in a host cell, where the method comprises growing a host culture having a plurality of host cells which contain one or more nucleic acids encoding a polypeptide which converts LA to GLA, wherein said one or more nucleic acids is operably associated with an expression control sequence, under conditions whereby said one or more nucleic acids are expressed, whereby GLA is produced in the host cell. In several preferred embodiments of the methods, the polypeptide employed in the method is a functionally active enzyme which desaturates a fatty acid molecule at carbon 6 from the carboxyl end of a fatty acid molecule; the said one or more nucleic acids is derived from a *Mortierella alpina*; the substrate for the polypeptide is exogenously supplied; the host cells are microbial cells; the microbial cells are yeast cells, such as Saccharomyces cells; and the growing conditions are inducible.

In another embodiment of the invention, a recombinant yeast cell is provided which converts Also provided is an oil comprising one or more PUFA, wherein the amount of said one or more PUFAs is approximately 0.3–30% arachidonic acid (ARA), approximately 0.2–30% dihomo-γ-linoleic acid (DGLA), and approximately 0.2–30% γ-linoleic acid (GLA). A preferred oil of the invention is one in which the ratio of ARA:DGLA:GLA is approximately 1.0:19.0:30 to 6.0:1.0:0.2. Another preferred embodiment of the invention is a pharmaceutical composition comprising the oils in a pharmaceutically acceptable carrier. Further provided is a nutritional composition comprising the oils of the invention. The nutritional compositions of the invention preferably are administered to a mammalian host parenterally or internally. A preferred composition of the invention for internal consumption is an infant formula. In a preferred embodiment, the nutritional compositions of the invention are in a liquid form or a solid form, and can be formulated in or as a dietary supplement, and the oils provided in encapsulated form. The oils of the invention can be free of particular components of other oils and can be derived from a microbial cell, such as a yeast cell.

The present invention further provides a method for desaturating a fatty acid. In a preferred embodiment the method comprises culturing a recombinant microbial cell according to the invention under conditions suitable for expression of a polypeptide encoded by said nucleic acid, wherein the host cell further comprises a fatty acid substrate of said polypeptide. Also provided is a fatty acid desaturated by such a method, and an oil composition comprising a fatty acid produced according to the methods of the invention.

BRIEF DESCRIPTION OF THE DRAWINGS

FIGS. 3A–E shows the DNA sequence of the *Mortierella alpina* Δ6-desaturase and the deduced amino acid sequence:

FIGS. 3A–E (SEQ ID NO 1 DELTA 6 DESATURASE cDNA)

FIGS. 3A–E (SEQ ID NO 2 DELTA 6 DESATURASE AMINO ACID)

FIG. 4 shows an alignment of a portion of the *Mortierella alpina* Δ6-desaturase amino acid sequence Ma 524 (SEQ ID NO:5), with other related sequences: ATTS4723 (SEQ ID NO:6), 12-5 (SEQ ID NO:7), T42806 (SEQ ID NO:8), W28140 (SEQ ID NO:9), R05219 (SEQ ID NO:10), W53753 (SEQ ID NO:11).

FIGS. 5A–D shows the DNA sequence of the *Mortierella alpina* Δ12-desaturase and the deduced amino acid sequence:

FIGS. 5A–D (SEQ ID NO 3 DELTA 12 DESATURASE cDNA)

FIGS. 5A–D (SEQ ID NO 4 DELTA 12 DESATURASE AMNO ACID).

BRIEF DESCRIPTION OF THE SEQUENCE LISTINGS

Figure 1:
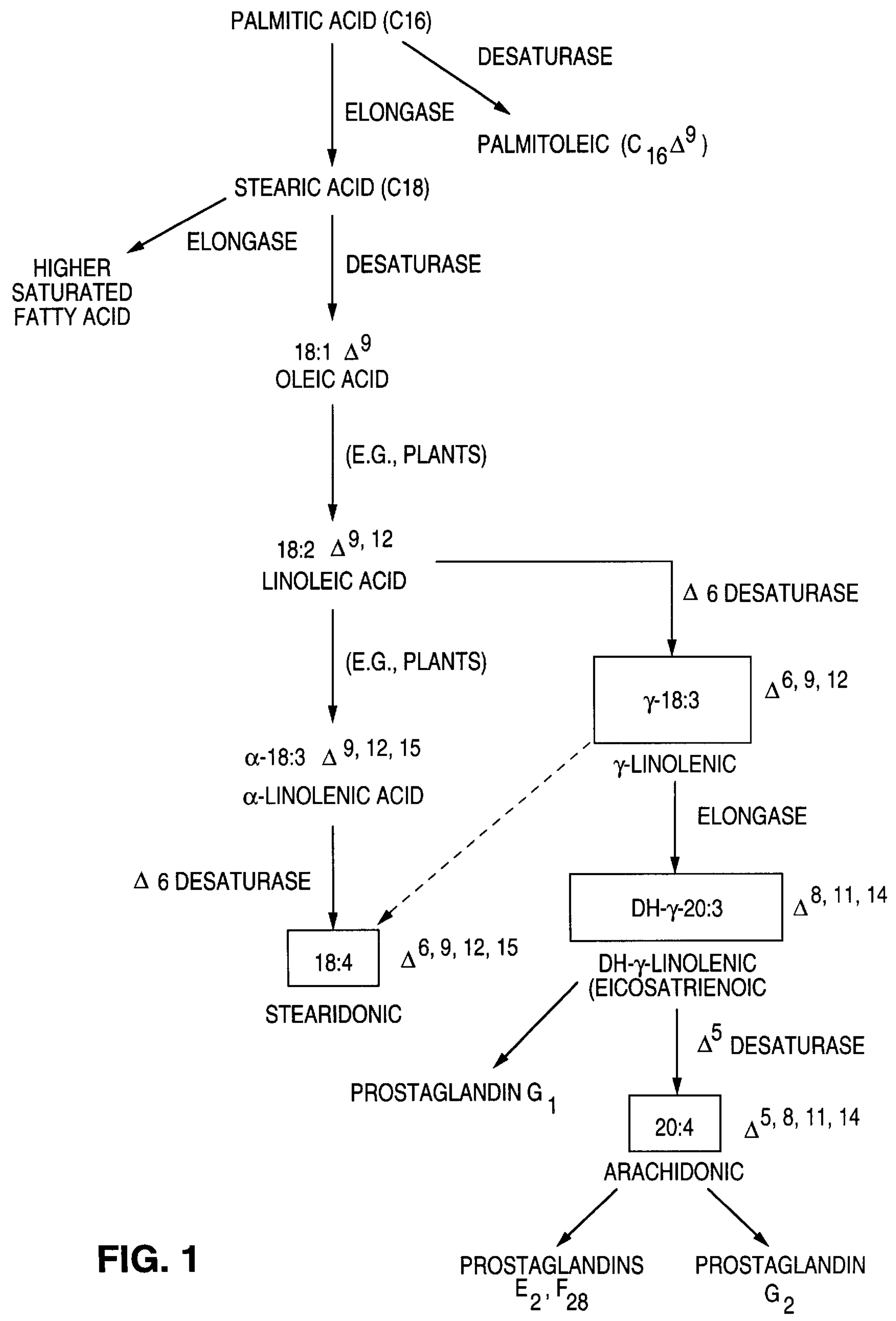
FIG. 1 shows possible pathways for the synthesis of arachidonic acid (20:4 $\Delta^{5,8,11,14}$) and stearidonic acid (18:4 $\Delta^{6,9,12,15}$) from palmitic acid ($C_{16}$) from a variety of organisms, including algae, Mortierella and humans. These PUFAs can serve as precursors to other molecules important for humans and other animals, including prostacyclins, leukotrienes, and prostaglandins, some of which are shown.

SEQ ID NO:1 shows the DNA sequence of the *Mortierella alpina* Δ6-desaturase.

SEQ ID NO:2 shows the protein sequence of the *Mortierella alpina* Δ6-desaturase.

SEQ ID NO:3 shows the DNA sequence of the *Mortierella alpina* Δ12-desaturase.

SEQ ID NO:4 shows the protein sequence of the *Mortierella alpina* Δ12-desaturase.

DESCRIPTION OF THE PREFERRED EMBODIMENTS

In accordance with the subject invention, novel DNA sequences, DNA constructs, methods and compositions are provided which permit modification of the poly-unsaturated long chain fatty acid content of, for example, microbial cells or animals. Host cells are manipulated to express a sense or antisense transcript of a DNA encoding a polypeptide(s) which catalyzes the desaturation of a fatty acid. The substrate(s) for the expressed enzyme may be produced by the host cell or may be exogenously supplied. To achieve expression, the transformed DNA is operably associated with transcriptional and translational initiation and termination regulatory regions that are functional in the host cell. Constructs comprising the gene to be expressed can provide for integration into the genome of the host cell or can autonomously replicate in the host cell. For production of linoleic acid (LA), the expression cassettes generally used include a cassette which provides for Δ12-desaturase activity, particularly in a host cell which produces or can take up oleic acid (U.S. Pat. No. 5,443,974). Production of LA also can be increased by providing an expression cassette for a Δ9-desaturase where that enzymatic activity is limiting. For production of ALA, the expression cassettes generally used include a cassette which provides for Δ15- or ω3-desaturase activity, particularly in a host cell which produces or can take up LA. For production of GLA or SDA, the expression cassettes generally used include a cassette which provides for Δ6-desaturase activity, particularly in a host cell which produces or can take up LA or ALA, respectively. Production of ω6-type unsaturated fatty acids, such as LA or GLA, is favored in a host microorganism or animal which is incapable of producing ALA. The host ALA production can be removed, reduced and/or inhibited by inhibiting the activity of a Δ15- or ω3- type desaturase (see FIG. 2). This can be accomplished by standard selection, providing an expression cassette for an antisense Δ15 or ω3 transcript, by disrupting a target Δ15- or ω3-desaturase gene through insertion, deletion, substitution of part or all of the target gene, or by adding an inhibitor of Δ15- or ω3-desaturase. Similarly, production of LA or ALA is favored in a microorganism or animal having Δ6-desaturase activity by providing an expression cassette for an antisense Δ6 transcript, by disrupting a Δ6-desaturase gene, or by use of a Δ6-desaturase inhibitor.

Microbial production of fatty acids has several advantages over purification from natural sources such as fish or plants. Many microbes are known with greatly simplified oil compositions compared with those of higher organisms, making purification of desired components easier. Microbial production is not subject to fluctuations caused by external variables such as weather and food supply. Microbially produced oil is substantially free of contamination by environmental pollutants. Additionally, microbes can provide PUFAs in particular forms which may have specific uses. For example, Spirulina can provide PUFAs predominantly at the first and third positions of triglycerides; digestion by pancreatic lipases preferentially releases fatty acids from these positions. Following human or animal ingestion of triglycerides derived from Spirulina, these PUFAs are released by pancreatic lipases as free fatty acids and thus are directly available, for example, for infant brain development. Additionally, microbial oil production can be manipulated by controlling culture conditions, notably by providing particular substrates for microbially expressed enzymes, or by addition of compounds which suppress undesired biochemical pathways. In addition to these advantages, production of fatty acids from recombinant microbes provides the ability to alter the naturally occurring microbial fatty acid profile by providing new synthetic pathways in the host or by suppressing undesired pathways, thereby increasing levels of desired PUFAs, or conjugated forms thereof, and decreasing levels of undesired PUFAs.

Production of fatty acids in animals also presents several advantages. Expression of desaturase genes in animals can produce greatly increased levels of desired PUFAs in animal tissues, making recovery from those tissues more economical. For example, where the desired PUFAs are expressed in the breast milk of animals, methods of isolating PUFAs from animal milk are well established. In addition to providing a source for purification of desired PUFAs, animal breast milk can be manipulated through expression of desaturase genes, either alone or in combination with other human genes, to provide animal milks substantially similar to human breast milk during the different stages of infant development. Humanized animal milks could serve as infant formulas where human nursing is impossible or undesired, or in cases of malnourishment or disease.

Depending upon the host cell, the availability of substrate, and the desired end product(s), several polypeptides, particularly desaturases, are of interest. By "desaturase" is intended a polypeptide which can desaturate one or more fatty acids to produce a mono- or poly-unsaturated fatty acid or precursor thereof of interest. Of particular interest are polypeptides which can catalyze the conversion of stearic acid to oleic acid, of oleic acid to LA, of LA to ALA, of LA to GLA, or of ALA to SDA, which includes enzymes which desaturate at the Δ9, Δ12, ω6, Δ15, ω3 or Δ6 positions. By "polypeptide" is meant any chain of amino acids, regardless of length or post-translational modification, for example, glycosylation or phosphorylation. Considerations for choosing a specific polypeptide having desaturase activity include the pH optimum of the polypeptide, whether the polypeptide is a rate limiting enzyme or a component thereof, whether the desaturase used is essential for synthesis of a desired poly-unsaturated fatty acid, and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_m$ and specific activity of the polypeptide in question therefore are considered in determining the suitability of a given polypeptide for modifying PUFA production in a given host cell. The polypeptide used in a particular situation is one which can function under the conditions present in the intended host cell but otherwise can be any polypeptide having desaturase activity which has the desired characteristic of being capable of modifying the relative production of a desired PUFA.

Figure 2:
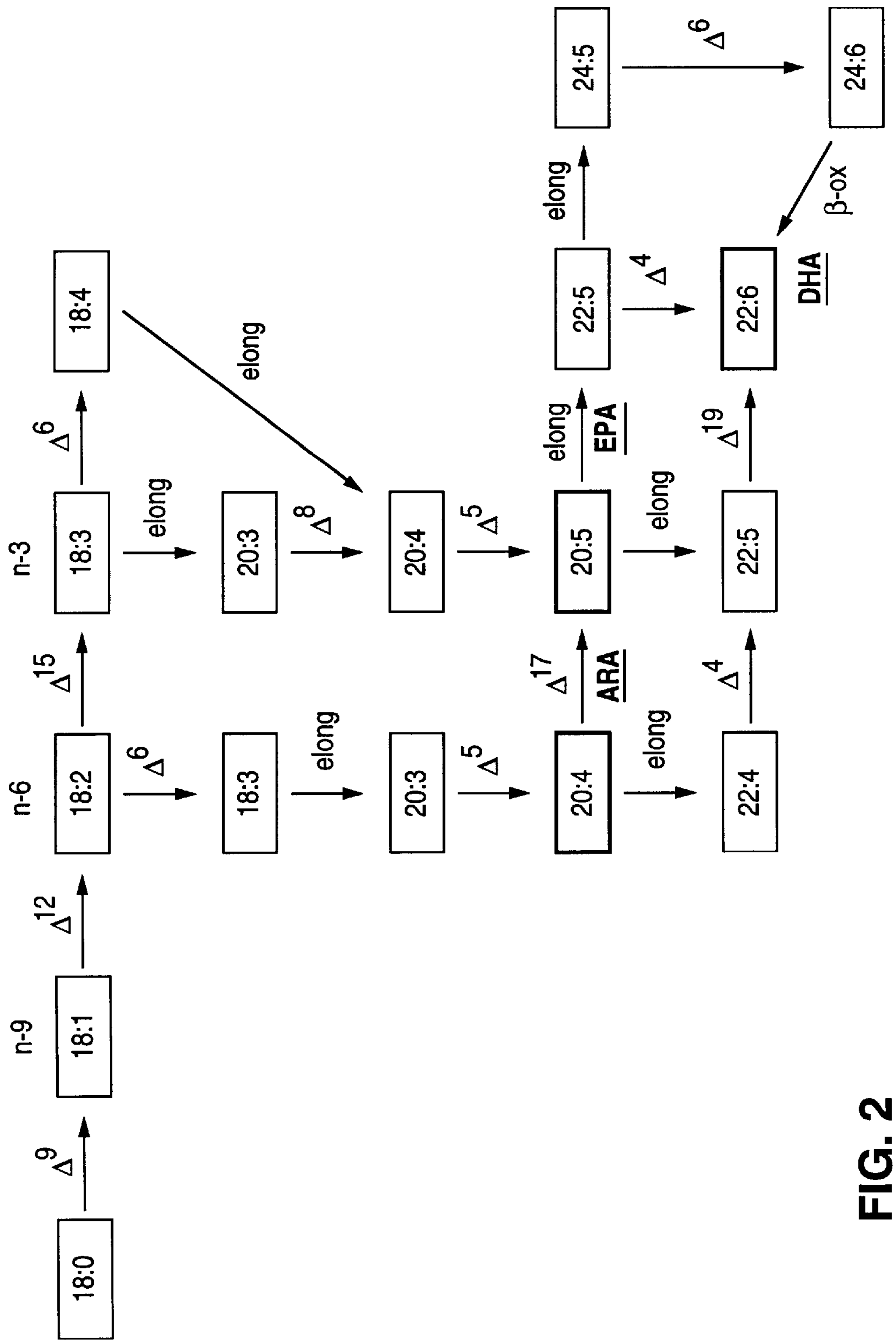
FIG. 2 shows possible pathways for production of PUFAs in addition to ARA, including EPA and DHA, again compiled from a variety of organisms.

For production of linoleic acid from oleic acid, the DNA sequence used encodes a polypeptide having Δ12-desaturase activity. For production of GLA from linoleic acid, the DNA sequence used encodes a polypeptide having Δ6-desaturase activity. In particular instances, expression of Δ6-desaturase activity can be coupled with expression of Δ12-desaturase activity and the host cell can optionally be depleted of any Δ15-desaturase activity present, for example by providing a transcription cassette for production of antisense sequences to the Δ15-desaturase transcription product, by disrupting the Δ15-desaturase gene, or by using a host cell which naturally has, or has been mutated to have, low Δ15-desaturase activity. Inhibition of undesired desaturase pathways also can be accomplished through the use of specific desaturase inhibitors such as those described in U.S. Pat. No. 4,778,630. Also, a host cell for Δ6-desaturase expression may have, or have been mutated to have, high Δ12-desaturase activity. The choice of combination of cassettes used depends in part on the PUFA profile and/or desaturase profile of the host cell. Where the host cell expresses Δ12-desaturase activity and lacks or is depleted in Δ15-desaturase activity, overexpression of Δ6-desaturase alone generally is sufficient to provide for enhanced GLA production. Where the host cell expresses Δ9-desaturase activity, expression of a Δ12- and a Δ6-desaturase can provide for enhanced GLA production. When Δ9-desaturase activity is absent or limiting, an expression cassette for Δ9-desaturase can be used. A scheme for the synthesis of arachidonic acid (20:4 $\Delta^{5,8,11,14}$) from stearic acid (18:0) is shown in FIG. 2. A key enzyme in this pathway is a Δ6-desaturase which converts the linoleic acid into γ-linolenic acid. Conversion of α-linolenic acid (ALA) to stearidonic acid by a Δ6-desaturase also is shown.

As a source of polypeptides having desaturase activity and oligonucleotides encoding such polypeptides are organisms which produce a desired poly-unsaturated fatty acid. As an example, microorganisms having an ability to produce GLA or ARA can be used as a source of Δ6- or Δ12-desaturase activity. Such microorganisms include, for example, those belonging to the genera Mortierella, Conidiobolus, Pythium, Phytophathora, Penicillium, Porphyridium, Coidosporium, Mucor, Fusarium, Aspergillus, Rhodotorula, and Entomophthora. Within the genus Porphyridium, of particular interest is *Porphyridium cruentum*. Within the genus Mortierella, of particular interest are *Mortierella elongata, Mortierella exigua, Mortierella hygrophila, Mortierella ramanniana*, var. angulispora, and *Mortierella alpina*. Within the genus Mucor, of particular interest are *Mucor circinelloides*and *Mucor javanicus*.

DNAs encoding desired desaturases can be identified in a variety of ways. As an example, a source of the desired desaturase, for example genomic or cDNA libraries from Mortierella, is screened with detectable enzymatically- or chemically-synthesized probes, which can be made from DNA, RNA, or non-naturally occurring nucleotides, or mixtures thereof. Probes may be enzymatically synthesized from DNAs of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

For the most part, some or all of the coding sequence for the polypeptide having desaturase activity is from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for flnction in the host cell, such as a longer half-life or a higher rate of production of a desired polyunsaturated fatty acid.

Of particular interest is the *Mortierella alpina* Δ6-desaturase, which has 457 amino acids and a predicted molecular weight of 51.8 kD; the amino acid sequence is shown in FIG. 3. The gene encoding the *Mortierella alpina* Δ6-desaturase can be expressed in transgenic microorganisms or animals to effect greater synthesis of GLA from linoleic acid or of stearidonic acid from ALA. Other DNAs which are substantially identical to the *Mortierella alpina* Δ6-desaturase DNA, or which encode polypeptides which are substantially identical to the *Mortierella alpina* Δ6-desaturase polypeptide, also can be used. By substantially identical is intended an amino acid sequence or nucleic acid sequence exhibiting in order of increasing preference at least 60%, 80%, 90% or 95% homology to the *Mortierella alpina* Δ6-desaturase amino acid sequence or nucleic acid sequence encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157: 105–132, 1982), or on the basis of the ability to assume similar polypeptide secondary structure (Chou and Fasman, *Adv. Enzymol.* 47: 45–148, 1978).

Also of interest is the *Mortierella alpina* Δ12-desaturase, the nucleotide and amino acid sequence of which is shown in FIG. 5. The gene encoding the *Mortierella alpina* Δ12-desaturase can be expressed in transgenic microorganisms or animals to effect greater synthesis of LA from oleic acid. Other DNAs which are substantially identical to the *Mortierella alpina* Δ12-desaturase DNA, or which encode polypeptides which are substantially identical to the *Mortierella alpina* Δ12-desaturase polypeptide, also can be used.

Encompassed by the present invention are related desaturases from the same or other organisms. Such related desaturases include variants of the disclosed Δ6- or Δ12-desaturase naturally occurring within the same or different species of Mortierella, as well as homologues of the disclosed Δ6- or Δ12-desaturase from other species. Also included are desaturases which, although not substantially identical to the *Mortierella alpina* Δ6- or Δ12-desaturase, desaturate a fatty acid molecule at carbon 6 or 12, respectively, from the carboxyl end of a fatty acid molecule, or at carbon 12 or 6 respectively terminal methyl carbon in an 18 carbon fatty acid molecule. Related desaturases can be identified by their ability to function substantially the same as the disclosed desaturases; that is, are still able to effectively convert LA to GLA, ALA to SDA or oleic acid to LA. Related desaturases also can be identified by screening sequence databases for sequences homologous to the disclosed desaturases, by hybridization of a probe based on the disclosed desaturases to a library constructed from the source organism, or by RT-PCR using mRNA from the source organism and primers based on the disclosed desaturases.

The regions of a desaturase polypeptide important for desaturase activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

Once the DNA encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the DNA encoding the desaturase polypeptide. Expression of the polypeptide coding region can take place in vitro or in a host cell. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell.

In vitro expression can be accomplished, for example, by placing the coding region for the desaturase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for the polypeptide, for example by determining its activity, or the synthesized polypeptide can be purified and then assayed.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source organism is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

When it is desirable to express more than one different gene, appropriate regulatory regions and expression methods, introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

As an example, where the host cell is a yeast, transcriptional and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al., *Mol. Cell. Biol.* Vol. 7, p. 3446, 1987; Johnston, *Microbiol. Rev.* Vol. 51, p. 458, 1987). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4.

Nucleotide sequences surrounding the translational initiation codon ATG have been found to affect expression in yeast cells. If the desired polypeptide is poorly expressed in yeast, the nucleotide sequences of exogenous genes can be modified to include an efficient yeast translation initiation sequence to obtain optimal gene expression. For expression in Saccharomyces, this can be done by site-directed mutagenesis of an inefficiently expressed gene by fusing it in-frame to an endogenous Saccharomyces gene, preferably a highly expressed gene, such as the lactase gene.

The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. Preferably, the termination region is derived from a yeast gene, particularly Saccharomyces, Schizosaccharomyces, Candida or Kluyveromyces. The 3' regions of two mammalian genes, γinterferon and α2 interferon, are also known to function in yeast.

Constructs comprising the gene of interest may be introduced into a host cell by standard techniques. These techniques include transformation, protoplast fusion, lipofection, transfection, transduction, conjugation, infection, bolistic impact, electroporation, microinjection, scraping, or any other method which introduces the gene of interest into the host cell. Methods of transformation which are used include lithium acetate transformation (*Methods in Enzymology*, Vol. 194, p. 186–187, 1991). For convenience, a host cell which has been manipulated by any method to take up a DNA sequence or construct will be referred to as "transformed" or "recombinant" herein.

The subject host will have at least have one copy of the expression construct and may have two or more, depending upon whether the gene is integrated into the genome, amplified, or is present on an extrachromosomal element having multiple copy numbers. Where the subject host is a yeast, four principal types of yeast plasmid vectors can be used: Yeast Integrating plasmids (YIps), Yeast Replicating plasmids (YRps), Yeast Centromere plasmids (YCps), and Yeast Episomal plasmids (YEps). YIps lack a yeast replication origin and must be propagated as integrated elements in the yeast genome. YRps have a chromosomally derived autonomously replicating sequence and are propagated as medium copy number (20 to 40), autonomously replicating, unstably segregating plasmids. YCps have both a replication origin and a centromere sequence and propagate as low copy number (10–20), autonomously replicating, stably segregating plasmids. YEps have an origin of replication from the yeast 2 μm plasmid and are propagated as high copy number, autonomously replicating, irregularly segregating plasmids. The presence of the plasmids in yeast can be ensured by maintaining selection for a marker on the plasmid. Of particular interest are the yeast vectors pYES2 (a YEp plasmid available from Invitrogen, confers uracil prototrophy and a GAL1 galactose-inducible promoter for expression), pRS425-pG1 (a YEp plasmid obtained from Dr. T. H. Chang, Ass. Professor of Molecular Genetics, Ohio State University, containing a constitutive GPD promoter and conferring leucine prototrophy), and pYX424 (a YEp plasmid having a constitutive TP1 promoter and conferring leucine prototrophy; Alber, T. and Kawasaki, G. (1982). *J Mol. & Appl. Genetics* 1: 419).

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host. Selection of a transformed host can also occur when the expressed marker protein can be detected, either directly or indirectly. The marker protein may be expressed alone or as a fusion to another protein. The marker protein can be detected by its enzymatic activity; for example βgalactosidase can convert the substrate X-gal to a colored product, and luciferase can convert luciferin to a light-emitting product. The marker protein can be detected by its light-producing or modifying characteristics; for example, the green fluorescent protein of *Aequorea Victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin and the amino glycoside G418 are of interest, as well as ability to grow on media lacking uracil, leucine, lysine or tryptophan.

Of particular interest is the Δ6- and Δ12-desaturase-mediated production of PUFAs in prokaryotic and eukaryotic host cells. Prokaryotic cells of interest include Eschericia, Bacillus, *Lactobacillus, cyanobacteria* and the like. Eukaryotic cells include mammalian cells such as those of lactating animals, avian cells such as of chickens, and other cells amenable to genetic manipulation including insect, fungal, and algae cells. The cells may be cultured or formed as part or all of a host organism including an animal. Viruses and bacteriophage also may be used with the cells in the production of PUFAs, particularly for gene transfer, cellular targeting and selection. In a preferred embodiment, the host is any microorganism or animal which produces and/or can assimilate exogenously supplied substrate(s) for a Δ6- and/or Δ12-desaturase, and preferably produces large amounts of one or more of the substrates. Examples of host animals include mice, rats, rabbits, chickens, quail, turkeys, bovines, sheep, pigs, goats, yaks, etc., which are amenable to genetic manipulation and cloning for rapid expansion of the transgene expressing population. For animals, the desaturase transgene(s) can be adapted for expression in target organelles, tissues and body fluids through modification of the gene regulatory regions. Of particular interest is the production of PUFAs in the breast milk of the host animal. Examples of host microorganisms include *Saccharomyces cerevisiae, Saccharomyces carlsbergensis*, or other yeast such as Candida, Kluyveromyces or other fungi, for example, filamentous fungi such as Aspergillus, Neurospora, Penicillium, etc. Desirable characteristics of a host microorganism are, for example, that it is genetically well characterized, can be used for high level expression of the product using ultra-high density fermentation, and is on the GRAS (generally recognized as safe) list since the proposed end product is intended for ingestion by humans. Of particular interest is use of a yeast, more particularly baker's yeast (*S. cerevisiae*), as a cell host in the subject invention. Strains of particular interest are SC334 (Mat αpep4-3 prbl-1122 ura3-52 leu2-3, 112 regl-501 gal1; *Gene* 83:57–64, 1989, Hovland P. et al.), YTC34 (αade2-101 his3Δ200 lys2-801 ura3-52; obtained from Dr. T. H. Chang, Ass. Professor of Molecular Genetics, Ohio State University), YTC41 (a/αura3-52/ura3=52 lys2-80 1/lys2-801 ade2-101/ade2-101 trpl-Δ/trpl-Δhis3Δ200/his3Δ200 leu2Δ1/leu2Δ1; obtained from Dr. T. H. Chang, Ass. Professor of Molecular Genetics, Ohio State University), BJ1995 (obtained from the Yeast Genetic Stock Centre, 1021 Donner Laboratory, Berkeley, Calif. 94720), INVSC1 (Mat αhiw3Δ1 leu2 trpl-289 ura3-52; obtained from Invitrogen, 1600 Faraday Ave., Carlsbad, Calif. 92008) and INVSC2 (Mat αhis3Δ200 ura3-167; obtained from Invitrogen).

For producing PUFAs in avian species and cells, such as chickens, turkeys, quail and ducks, gene transfer can be performed by introducing a nucleic acid sequence encoding a Δ6 and/or Δ12-desaturase into the cells following procedures known in the art. If a transgenic animal is desired, pluripotent stem cells of embryos can be provided with a vector carrying a desaturase encoding transgene and developed into adult animal (U.S. Pat. No. 5,162,215; Ono et al. (1996) Comparative *Biochemistry and Physiology A* 113(3):287–292; WO 9612793; WO 9606160). In most cases, the transgene will be modified to express high levels of the desaturase in order to increase production of PUFAs. The transgene can be modified, for example, by providing transcriptional and/or translational regulatory regions that function in avian cells, such as promoters which direct expression in particular tissues and egg parts such as yolk. The gene regulatory regions can be obtained from a variety of sources, including chicken anemia or avian leukosis viruses or avian genes such as a chicken ovalbumin gene.

Production of PUFAs in insect cells can be conducted using baculovirus expression vectors harboring one or more desaturase transgenes. Baculovirus expression vectors are available from several commercial sources such as Clonetech. Methods for producing hybrid and transgenic strains of algae, such as marine algae, which contain and express a desaturase transgene also are provided. For example, transgenic marine algae may be prepared as described in U.S. Pat. No. 5,426,040. As with the other expression systems described above, the timing, extent of expression and activity of the desaturase transgene can be regulated by fitting the polypeptide coding sequence with the appropriate transcriptional and translational regulatory regions selected for a particular use. Of particular interest are promoter regions which can be induced under preselected growth conditions. For example, introduction of temperature sensitive and/or metabolite responsive mutations into the desaturase transgene coding sequences, its regulatory regions, and/or the genome of cells into which the transgene is introduced can be used for this purpose.

The transformed host cell is grown under appropriate conditions adapted for a desired end result. For host cells grown in culture, the conditions are typically optimized to produce the greatest or most economical yield of PUFAs, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection. Microorganisms of interest, such as yeast are preferably grown in selected medium. For yeast, complex media such as peptone broth (YPD) or a defined media such as a minimal media (contains amino acids, yeast nitrogen base, and ammonium sulfate, and lacks a component for selection, for example uracil) are preferred. Desirably, substrates to be added are first dissolved in ethanol. Where necessary, expression of the polypeptide of interest may be induced, for example by including or adding galactose to induce expression from a GAL promoter.

Expression in cells of a host animal can likewise be accomplished in a transient or stable manner. Transient expression can be accomplished via known methods, for example infection or lipofection, and can be repeated in order to maintain desired expression levels of the introduced construct (see Ebert, PCT publication WO 94/05782). Stable expression can be accomplished via integration of a construct into the host genome, resulting in a transgenic animal. The construct can be introduced, for example, by microinjection of the construct into the pronuclei of a fertilized egg, or by transfection, retroviral infection or other techniques whereby the construct is introduced into a cell line which may form or be incorporated into an adult animal (U.S. Pat. No. 4,873,191; U.S. Pat. No. 5,530,177; U.S. Pat. No. 5,565,362; U.S. Pat. No. 5,366,894; Willmut et al (1997) Nature 385:810). The recombinant eggs or embryos are transferred to a surrogate mother (U.S. Pat. No. 4,873,191; U.S. Pat. No. 5,530,177; U.S. Pat. No. 5,565,362; U.S. Pat. No. 5,366,894; Wilmut et al (supra)).

After birth, transgenic animals are identified, for example, by the presence of an introduced marker gene, such as for coat color, or by PCR or Southern blotting from a blood, milk or tissue sample to detect the introduced construct, or by an immunological or enzymological assay to detect the expressed protein or the products produced therefrom (U.S. Pat. No. 4,873,191; U.S. Pat. No. 5,530,177; U.S. Pat. No. 5,565,362; U.S. Pat. No. 5,366,894; Wilmut et al (supra)). The resulting transgenic animals may be entirely transgenic or may be mosaics, having the transgenes in only a subset of their cells. The advent of mammalian cloning, accomplished by fusing a nucleated cell with an enucleated egg, followed by transfer into a surrogate mother, presents the possibility of rapid, large-scale production upon obtaining a "founder" animal or cell comprising the introduced construct; prior to this, it was necessary for the transgene to be present in the germ line of the animal for propagation (Wilnut et al (supra)).

Expression in a host animal presents certain efficiencies, particularly where the host is a domesticated animal. For production of PUFAs in a fluid readily obtainable from the host animal, such as milk, the desaturase transgene can be expressed in mammary cells from a female host, and the PUFA content of the host cells altered. The desaturase transgene can be adapted for expression so that it is retained in the mammary cells, or secreted into milk, to form the PUFA reaction products localized to the milk (PCT publication WO 95/24488). Expression can be targeted for expression in mammary tissue using specific regulatory sequences, such as those of bovine α-lactalbumin, α-casein, β-casein, γ-casein, κ-casein, β-lactoglobulin, or whey acidic protein, and may optionally include one or more introns and/or secretory signal sequences (U.S. Pat. No. 5,530,177; Rosen, U.S. Pat. No. 5,565,362; Clark et al., U.S. Pat. No. 5,366,894; Garner et al., PCT publication WO 95/23868). Expression of desaturase transgenes, or antisense desaturase transcripts, adapted in this manner can be used to alter the levels of specific PUFAs, or derivatives thereof, found in the animals milk. Additionally, the desaturase transgene(s) can be expressed either by itself or with other transgenes, in order to produce animal milk containing higher proportions of desired PUFAs or PUFA ratios and concentrations that resemble human breast milk (Prieto et al., PCT publication WO 95/24494).

The desaturated fatty acids may be found in the host microorganism or animal as free fatty acids or in conjugated forms such as acylglycerols, phospholipids, sulfolipids or glycolipids, and may be extracted from the host cell through a variety of means well-known in the art. Such means may include extraction with organic solvents, sonication, supercritical fluid extraction using for example carbon dioxide, and physical means such as presses, or combinations thereof. Of particular interest is extraction with methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing GLA, SDA, ARA, DHA and EPA may be accomplished by treatment with urea and/or fractional distillation.

The subject invention finds many applications. Probes based on the DNAs of the present invention may find use in methods for isolating related molecules or in methods to detect organisms expressing desaturases. When used as probes, the DNAs or oligonucleotides must be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

The PUFAs, or derivatives thereof, made by the disclosed method can be used as dietary substitutes, or supplements, particularly infant formulas, for patients undergoing intravenous feeding or for preventing or treating malnutrition. Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. Additionally, the predominant triglyceride in human milk has been reported to be 1,3-di-oleoyl-2-palmitoyl, with 2-palmitoyl glycerides reported as better absorbed than 2-oleoyl or 2-lineoyl glycerides (U.S. Pat. No. 4,876,107). Thus, fatty acids such as ARA, DGLA, GLA and/or EPA produced by the invention can be used to alter the composition of infant formulas to better replicate the PUFA composition of human breast milk. In particular, an oil composition for use in a pharmacologic or food supplement, particularly a breast milk substitute or supplement, will preferably comprise one or more of ARA, DGLA and GLA. More preferably the oil will comprise from about 0.3 to 30% ARA, from about 0.2 to 30% DGL, and from about 0.2 to about 30% GLA. In addition to the concentration, the ratios of ARA, DGLA and GLA can be adapted for a particular given end use. When formulated as a breast milk supplement, an oil composition which contains two or more of ARA, DGLA and GLA will be provided in a ratio of about 1:19:30 to about 6:1:0.2, respectively. For example, the breast milk of animals can vary in ratios of ARA, DGLA and DGL ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to ARA can be used to precisely control the PUFA ratios. For example, a 5% to 10% conversion rate of DGLA to ARA can be used to produce an ARA to DGLA ratio of about 1:19, whereas a conversion rate of about 75% to 80% can be used to produce an ARA to DGLA ratio of about 6:1. Therefore, whether in a cell culture system or in a host animal, regulating the timing, extent and specificity of desaturase expression as described can be used to modulate the PUFA levels and ratios. And depending on the expression system, e.g., cell culture and animal expressing oil(s) in their milk, the oils also can be isolated and recombined in the desired concentrations and ratios. Amounts of oils providing these ratios of PUFA can be determined following standard protocols. PUFAs, or host cells containing them, also can be used as animal food supplements to alter an animal's tissue or milk fatty acid composition to one more desirable for human or animal consumption.

For dietary supplementation, the purified PUFAs, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

For pharmaceutical use (human or veterinary), the compositions are generally administered orally but can be administered by any route by which they may be successfully absorbed, e.g., parenterally (i.e. subcutaneously, intramuscularly or intravenously), rectally or vaginally or topically, for example, as a skin ointment or lotion. The PUFAs of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids. The typical normal adult plasma fatty acid profile comprises 6.64 to 9.46% of ARA, 1.45 to 3.11% of DGLA, and 0.02 to 0.08% of GLA. These PUFAs or their metabolic precursors can be administered, either alone or in mixtures with other PUFAs, to achieve a normal fatty acid profile in a patient. Where desired, the individual components of formulations may be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention; preferred is a composition having from about 1 to about 25 weight percent of the total PUFA composition as GLA (U.S. Pat. No. 5,196,198). Other vitamins, and particularly fat-soluble vitamins such as vitamin A, D, E and L-carnitine can optionally be included. Where desired, a preservative such as a tocopherol may be added, typically at about 0.1% by weight.

The following examples are presented by way of illustration, not of limitation.

EXAMPLES

Example 1 Construction of a cDNA Library from *Mortierella alpina*

Example 2 Isolation of a Δ6-desaturase Nucleotide Sequence from *Mortierella alpina*

Example 3 Identification of Δ6-desaturases Homologous to the *Mortierella alpina* Δ6-desaturase Example 4 Isolation of a Δ12-desaturase Nucleotide Sequence from *Motierella Alpina*

Example 5 Expression of *M. alpina* Desaturase Clones in Baker's Yeast

Example 6 Initial Optimization of Culture Conditions

Example 7 Distribution of PUFAs in Yeast Lipid Fractions

Example 8 Further Culture Optimization and Coexpression of Δ6 and Δ12-desaturases

Example 1

Construction of a cDNA Library from *Mortierella alpina*

Total RNA was isolated from a 3 day old PUFA-producing culture of *Mortierella alpina* using the protocol of Hoge et al. (1982) *Experimental Mycology* 6:225–232. The RNA was used to prepare double-stranded cDNA using BRL's lambda-ZipLox system following the manufactur's instructions. Several size fractions of the *M. alpina* cDNA were packaged separately to yield libraries with different average-sized inserts. A "full-length" library contains approximately 3x106 clones with an average insert size of 1.77 kb. The "sequencing-grade" library contains approximately $6\times10^5$ clones with an average insert size of 1.1 kb.

Example 2

Isolation of a Δ6-desaturase Nucleotide Sequence from *Motierella Alpina*

A nucleic acid sequence from a partial cDNA clone, Ma524, encoding a Δ6 fatty acid desaturase from *Mortierella alpina* was obtained by random sequencing of clones from the *M. alpina* cDNA sequencing grade library described in Example 1. cDNA-containing plasmids were excised as follows:

Five μl of phage were combined with 100 μl of *E. coli* DH10B(ZIP) grown in ECLB plus 10 μg/ml kanamycin, 0.2% maltose, and 10 mM $MgSO_4$ and incubated at 37 degrees for 15 minutes. 0.9 ml SOC was added and 100 μl of the bacteria immediately plated on each of 10 ECLB+50 μg Pen plates. No 45 minute recovery time was needed. The plates were incubated overnight at 37°. Colonies were picked into ECLB+50 μg Pen media for overnight cultures to be used for making glycerol stocks and miniprep DNA. An aliquot of the culture used for the miniprep is stored as a glycerol stock. Plating on ECLB+50 μg Pen/ml resulted in more colonies and a greater proportion of colonies containing inserts than plating on 100 μg/ml Pen.

Random colonies were picked and plasmid DNA purified using Qiagen miniprep kits. DNA sequence was obtained from the 5' end of the cDNA insert and compared to the National Center for Biotechnology Information (NCBI) nonredundant database using the BLASTX algorithm. Ma524 was identified as a putative desaturase based on DNA sequence homology to previously identified desaturases.

A full-length cDNA clone was isolated from the *M.alpina* full-length library and designated pCGN5532. The cDNA is contained as a 1617 bp insert in the vector pZL1 (BRL) and, beginning with the first ATG, contains an open reading frame encoding 457 amino acids. The three conserved "histidine boxes" known to be conserved among membrane-bound deaturases (Okuley, et al. (1994) *The Plant Cell* 6:147–158) were found to be present at amino acid positions 172–176, 209–213, and 395–399 (see FIG. 3). As with other membrane-bound Δ6-desaturases the final HXXHH histidine box motif was found to be QXXHH. The amino acid sequence of Ma524 was found to display significant homology to a portion of a *Caenorhabditis elegans* cosmid, WO6D2.4, a cytochrome b5/desaturase fusion protein from sunflower, and the Synechocystis and Spirulina Δ6-desaturases. In addition, Ma524 was shown to have homology to the borage Δ6-desaturase amino sequence (PCT publication W) 96/21022). Ma524 thus appears to encode a Δ6-desaturase that is related to the borage and algal Δ6-desaturases.

Surprisingly, the amino terminus of the encoded protein was found to exhibit significant homology to cytochrome b5 proteins. The Mortierella cDNA clone appears to represent a fusion between a cytochrome b5 and a fatty acid desaturase. Since cytochrome b5 is believed to function as the electron donor for membrane-bound desaturase enzymes, it is possible that the N-terminal cytochrome b5 domain of this desaturase protein is involved in its function. This may be advantageous when expressing the desaturase in heterologous systems for PUFA production. However, it should be noted that, although the amino acid sequences of Ma524 and the borage Δ6 were found to contain regions of homology, the base compositions of the cDNAs were shown to be significantly different. For example, the borage cDNA was shown to have an overall base composition of 60% A/T, with some regions exceeding 70%, while Ma524 was shown to have an average of 44% A/T base composition, with no regions exceeding 60%. This may have implications for expressing the cDNAs in microorganisms or animals which favor different base compositions. It is known that poor expression of recombinant genes can occur when the host prefers a base composition different from that of the introduced gene. Mechanisms for such poor expression include decreased stability, cryptic splice sites, and/or translatability of the mRNA and the like.

Example 3

Identification of Δ6-desaturases Homologous to the *Mortierella alpina* Δ6-desaturase Nucleic acid sequences that encode putative Δ6-desaturases were identified through a BLASTX search of the Expressed Sequence Tag ("EST") databases through NCBI using the Ma524 amino acid sequence. Several sequences showed significant homology. In particular, the deduced amino acid sequence of two *Arabidopsis thalian* sequences, (accession numbers F1 3728 and T42806) showed homology to two different regions of the deduced amino acid sequence of Ma524. The following PCR primers were designed: ATTS4723-FOR (complementary to F13728) 5' CUACUACUACUAGGAGTCCTCTACGGT-GTTTTG (SEQ ID NO:13) and T42806-REV (complementary to T42806) 5° CAUCAUCAUCAUAT-GATGCTCAAGCTGAAACTG. (SEQ ID NO:14) Five μg of total RNA isolated from developing siliques of *Arabidopsis thalian* was reverse transcribed using BRL Superscript RTase and the primer TSyn (5'-CCAAGCTTCTGCAGGAGCTCTTTTTTTTTTTTTTT-3'). (SEQ ID NO:12) PCR was carried out in a 50 ul volume containing: template derived from 25 ng total RNA, 2 pM each primer, 200 μM each deoxyribonucleotide triphosphate, 60 mM Tris-C1, pH 8.5, 15 mM $(NH_4)_2SO_4$, 2 mM $MgCl_2$, 0.2 U Taq Polymerase. Thermocycler conditions were as follows: 94 degrees for 30 sec., 50 degrees for 30 sec., 72 degrees for 30 sec. PCR was continued for 35 cycles followed by an additional extension at 72 degrees for 7 minutes. PCR resulted in a fragment of approximately ~750 base pairs which was subcloned, named 12-5, and sequenced. Each end of this fragment was formed to correspond to the Arabidopsis ESTs from which the PCR primers were designed. The putative amino acid sequence of 12-5 was compared to that of Ma524, and ESTs from human (W28140), mouse (W53753), and *C. elegans* (R05219) (see FIG. 4). Homology patterns with the Mortierella Δ6- desaturase indicate that these sequences represent putative desaturase polypeptides. Based on this experiment approach, it is likely that the full-length genes can be cloned using probes based on the EST sequences. Following the cloning, the genes can then be placed into expression vectors, expressed in host cells, and their specific Δ6- or other desaturase activity can be determined as described below.

Example 4

Isolation of a Δ12-desaturase Nucleotide Sequence from *Motierella Alpina*

Based on the fatty acids it accumulates, it seemed probable that *Mortierella alpina* has an ω6 type desaturase. The ω6-desaturase is responsible for the production of linoleic acid (18:2) from oleic acid (18:1). Linoleic acid (18:2) is a substrate for a Δ6-desaturase. This experiment was designed to determine if *Mortierella alpina* has a Δ12-desaturase polypeptide, and if so, to identify the corresponding nucleotide sequence.

A random colony from the *M. alpina* sequencing grade library, Ma648, was sequenced and identified as a putative desaturase based on DNA sequence homology to previously identified desaturases, as described for Ma524 (see Example 2). The deduced amino acid sequence from the 5' end of the Ma648 cDNA displays significant homology to soybean microsomal ω6 (Δ12) desaturase (accession #L43921) as well as castor bean oleate 12-hydroxylase (accession #U22378). In addition, homology was observed when compared to a variety of other ω6 (Δ12) and c03 (Δ5) fatty acid desaturase sequences.

Example 5

Expression of *M Alpina* Desaturase Clones in Baker's Yeast

Yeast Transformation

Lithium acetate transformation of yeast was performed according to standard protocols (*Methods in Enzymology*, Vol. 194, p. 186–187, 1991). Briefly, yeast were grown in YPD at 30° C. Cells were spun down, resuspended in TE, spun down again, resuspended in TE containing 100 mM lithium acetate, spun down again, and resuspended in TE/lithium acetate. The resuspended yeast were incubated at 30° C. for 60 minutes with shaking. Carrier DNA was added, and the yeast were aliquoted into tubes. Transforming DNA was added, and the tubes were incubated for 30 min. at 30° C. PEG solution (35% (w/v) PEG 4000, 100 mM lithium acetate, TE pH7.5) was added followed by a 50 min. incubation at 30° C. A 5 min. heat shock at 42° C. was performed, the cells were pelleted, washed with TE, pelleted again and resuspended in TE. The resuspended cells were then plated on selective media.

Desaturase Expression in Transformed Yeast cDNA clones from *Mortierella alpina* were screened for desaturase activity in baker's yeast. A canola A15-desaturase (obtained by PCR using $1^{st}$ strand cDNA from *Brassica napus* cultivar 212/86 seeds using primers based on the published sequence (Arondel et al. *Science* 258:1353–1355)) was used as a positive control. The Δ15-desaturase gene and the gene from cDNA clones Ma524 and Ma648 were put in the expression vector pYES2 (Invitrogen), resulting in plasmids pCGR-2, pCGR-5 and pCGR-7, respectively. These plasmids were transfected into *S. cerevisiae* yeast strain 334 and expressed after induction with galactose and in the presence of substrates that allowed detection of specific desaturase activity. The control strain was *S. cerevisiae* strain 334 containing the unaltered pYES2 vector. The substrates used, the products produced and the indicated desaturase activity were: DGLA (conversion to ARA would indicate Δ5-desaturase activity), linoleic acid (conversion to GLA would indicate Δ6-desaturase activity; conversion to ALA would indicate Δ15-desaturase activity), oleic acid (an endogenous substrate made by *S. cerevisiae*, conversion to linoleic acid would indicate Δ12-desaturase activity, which *S. cerevisiae* lacks), or ARA (conversion to EPA would indicate Δ17-desaturase activity).

Cultures were grown for 48–52 hours at 15° C. in the presence of a particular substrate. Lipid fractions were extracted for analysis as follows: Cells were pelleted by centrifugation, washed once with sterile $ddH_20$, and repelleted. Pellets were vortexed with methanol; chloroform was added along with tritridecanoin (as an internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were then derivatized to fatty acid methyl esters (FAME) for gas chromatography analysis (GC) by adding 2 ml of 0.5 N potassium hydroxide in methanol to a closed tube. The samples were heated to 95° C. to 100° C. for 30 minutes and cooled to room temperature. Approximately 2 ml of 14% boron trifluoride in methanol was added and the heating repeated. After the extracted lipid mixture cooled, 2 ml of water and 1 ml of hexane were added to extract the FAME for analysis by GC. The percent conversion was calculated by dividing the product produced by the sum of (the product produced and the substrate added) and then multiplying by 100. To calculate the oleic acid percent conversion, as no substrate was added, the total linoleic acid produced was divided by the sum of oleic acid and linoleic acid produced, then multiplying by 100. The desaturase activity results are provided in Table 1 below.

TABLE 1

*M. Alpina* Desaturase Expression in Baker's Yeast

| CLONE | ENZYME ACTIVITY | % CONVERSION OF SUBSTRATE |
|---|---|---|
| pCGR-2 | Δ6 | 0 (18:2 to 18:3w6) |
| (canola Δ15 | Δ15 | 16.3 (18:2 to 18:3w3) |
| desaturase) | Δ5 | 2.0 (20:3 to 20:4w6) |
| | Δ17 | 2.8 (20:4 to 20:5w3) |
| | Δ12 | 1.8 (18:1 to 18:2w6) |
| pCGR-5 | Δ6 | 6.0 |
| (*M. alpina* | Δ15 | 0 |
| Ma 524 | Δ5 | 2.1 |
| | Δ17 | 0 |
| | Δ12 | 3.3 |
| pCGR-7 | Δ6 | 0 |
| (*M. alpina* | Δ15 | 3.8 |
| Ma648 | Δ5 | 2.2 |
| | Δ17 | 0 |
| | Δ12 | 63.4 |

The Δ15-desaturase control clone exhibited 16.3% conversion of the substrate. The pCGR-5 clone expressing the Ma524 cDNA showed 6% conversion of the substrate to GLA, indicating that the gene encodes a Δ6-desaturase. The pCGR-7 clone expressing the Ma648 cDNA converted 63.4% conversion of the substrate to LA, indicating that the gene encodes a Δ12-desaturase. The background (non-specific conversion of substrate) was between 0–3% in these cases. We also found substrate inhibition of the activity by using different concentrations of the substrate. When substrate was added to 100 μM, the percent conversion to product dropped compared to when substrate was added to 25 μM (see below). Additionally, by varying the substrate concentration between 5 μM and 200 μM, conversion ratios were found to range between about 5% to about 75% greater. These data show that desaturases with different substrate specificities can be expressed in a heterologous system and used to produce poly-unsaturated long chain fatty acids.

Table 2 represents fatty acids of interest as a percent of the total lipid extracted from the yeast host *S. cerevisiae* 334 with the indicated plasmid. No glucose was present in the growth media. Affinity gas chromatography was used to separate the respective lipids. GC/MS was employed to verify the identity of the product(s). The expected product for the *B. napus* Δ15-desaturase, α-linolenic acid, was detected when its substrate, linoleic acid, was added exogenously to the induced yeast culture. This finding demonstrates that yeast expression of a desaturase gene can produce functional enzyme and detectable amounts of product under the current growth conditions. Both exogenously added substrates were taken up by yeast, although slightly less of the longer chain PUFA, dihomo-γ-linolenic acid (20:3), was incorporated into yeast than linoleic acid (18:2) when either was added in free form to the induced yeast cultures. γ-linolenic acid was detected when linoleic acid was present during induction and expression of *S. cerevisiae* 334 (pCGR-5). The presence of this PUFA demonstrates Δ6-desaturase activity from pCGR-5 (MA524). Linoleic acid, identified in the extracted lipids from expression of *S. cerevisiae* 334 (pCGR-7), classifies the cDNA MA648 from *M. alpina* as the Δ12-desaturase.

fatty acid substrate concentration was well illustrated when the percent conversion rates of the respective fatty acid substrates to their respective products were compared in Table 3B. In all cases, 100 μM substrate concentration in the growth media decreased the percent conversion to product. The uptake of α-linolenic was comparable to other PUFAs added in free form, while the Δ6-desaturase percent conversion, 3.8–17.5%, to the product stearidonic acid was the lowest of all the substrates examined (Table 3B). The effect of media, such as YPD (rich media) versus minimal media with glucose on the conversion rate of Δ12-desaturase was dramatic. Not only did the conversion rate for oleic to linoleic acid drop, (Table 3B) but the percent of linoleic acid formed also decreased by 11% when rich media was used for growth and induction of yeast desaturase Δ12 expression (Table 3A). The effect of media composition was also evident when glucose was present in the growth media for Δ6-desaturase, since the percent of substrate uptake was decreased at 25 μM (Table 3A). However, the conversion rate remained the same and percent product formed decreased for Δ6-desaturase for in the presence of glucose.

TABLE 2

Fatty Acid as a Percentage of Total Lipid Extracted from Yeast

| Plasmid in Yeast (enzyme) | 18:2 Incorporated | α-18:3 Produced | γ-18:3 Produced | 20:3 Incorporated | 20:4 Produced | 18:1* Present | 18:2 Produced |
|---|---|---|---|---|---|---|---|
| pYES2 (control) | 66.9 | 0 | 0 | 58.4 | 0 | 4 | 0 |
| pCGR-2 (Δ15) | 60.1 | 5.7 | 0 | 50.4 | 0 | 0.7 | 0 |
| pCGR-5 (Δ6) | 62.4 | 0 | 4.0 | 49.9 | 0 | 2.4 | 0 |
| pCGR-7 (Δ12) | 65.6 | 0 | 0 | 45.7 | 0 | 7.1 | 12.2 |

100 μM substrate added
*18:1 is an endogenous fatty acid in yeast
Key To Tables
18:1 = oleic acid
18:2 = linoleic acid
α-18:3 = α-linolenic acid
γ-18:3 = γ-linolenic acid
18:4 = stearidonic acid
20:3 = dihomo-γ-linolenic acid
20:4 = arachidonic acid Example 6

Optimization of Culture Conditions

Table 3A shows the effect of exogenous free fatty acid substrate concentration on yeast uptake and conversion to fatty acid product as a percentage of the total yeast lipid extracted. In all instances, low amounts of exogenous substrate (1–10 μM) resulted in low fatty acid substrate uptake and product formation. Between 25 and 50 μM concentration of free fatty acid in the growth and induction media gave the highest percentage of fatty acid product formed, while the 100 μM concentration and subsequent high uptake into yeast appeared to decrease or inhibit the desaturase activity. The amount of fatty acid substrate for yeast expressing Δ12-desaturase was similar under the same growth conditions, since the substrate, oleic acid, is an endogenous yeast fatty acid. The use of a-linolenic acid as an additional substrate for pCGR-5 (Δ6) produced the expected product, stearidonic acid (Table 3A). The feedback inhibition of high

TABLE 3A

Effect of Added Substrate on the Percentage of Incorporated Substrate and Product Formed in Yeast Extracts

| Plasmid in Yeast | pCGR-2 (Δ15) | PcGR-5 (Δ6) | pCGR-5 (Δ6) | pCGR-7 (Δ12) |
|---|---|---|---|---|
| substrate/product | 18:2/α-18:3 | 18:2/γ-18:3 | α-18:3/18:4 | 18:1*/18:2 |
| 1 μM sub. | ND | 0.9/0.7 | ND | ND |
| 10 μM sub. | ND | 4.2/2.4 | 10.4/2.2 | ND |
| 25 μM sub. | ND | 11/3.7 | 18.2/2.7 | ND |
| 25 μM◇ sub. | 36.6/7.2◇ | 25.1/10.3◇ | ND | 6.6/15.8◇ |
| 50 μM sub. | 53.1/6.5◇ | ND | 36.2/3 | 10.8/13+ |
| 100 μM sub. | 60.1/5.7◇ | 62.4/4◇ | 47.7/1.9 | 10/24.8 |

TABLE 3B

Effect of Substrate Concentration in Media on the Percent Conversion of Fatty Acid Substrate to Product in Yeast Extracts

| Plasmid in Yeast | pCGR-2 (Δ15) | pCGR-5 (Δ6) | pCGR-5 (Δ6) | pCGR-7 (Δ12) |
|---|---|---|---|---|
| substrate → product | 18:2 → α-18:3 | 18:2 → γ18:3 | α-18:3 → 18:4 | 18:1* → 18:2 |
| 1 μM sub. | ND | 43.8 | ND | ND |
| 10 μM sub. | ND | 36.4 | 17.5 | ND |
| 25 μM sub. | ND | 25.2 | 12.9 | ND |
| 25 μM◇ sub. | 16.4◇ | 29.1◇ | ND | 70.5◇ |
| 50 μM sub. | 10.9◇ | ND | 7.7 | 54.6+ |
| 100 μM sub. | 8.7◇ | 6◇ | 3.8 | 71.3 |

◇ no glucose in media
+Yeast peptone broth (YPD)
*18:1 is an endogenous yeast lipid
sub. is substrate concentration
ND (not done)

Table 4 shows the amount of fatty acid produced by a recombinant desaturase from induced yeast cultures when different amounts of free fatty acid substrate were used. Fatty acid weight was determined since the total amount of lipid varied dramatically when the growth conditions were changed, such as the presence of glucose in the yeast growth and induction media. To better determine the conditions when the recombinant desaturase would produce the most PUFA product, the quantity of individual fatty acids were examined. The absence of glucose dramatically reduced by three fold the amount of linoleic acid produced by recombinant Δ12-desaturase. For the Δ12-desaturase the amount of total yeast lipid was decreased by almost half in the absence of glucose. Conversely, the presence of glucose in the yeast growth media for Δ6-desaturase drops the γ-linolenic acid produced by almost half, while the total amount of yeast lipid produced was not changed by the presence/absence of glucose. This points to a possible role for glucose as a modulator of Δ6-desaturase activity.

TABLE 4

Fatty Acid Produced in μg from Yeast Extracts

| Plasmid in Yeast (enzyme) | pCGR-5 (Δ6) | pCGR-5 (Δ6) | pCGR-7 (Δ12) |
|---|---|---|---|
| product | γ-18:3 | 18:4 | 18:2* |
| 1 μM sub. | 1.9 | ND | ND |
| 10 μM sub. | 5.3 | 4.4 | ND |

TABLE 4-continued

Fatty Acid Produced in μg from Yeast Extracts

| Plasmid in Yeast (enzyme) | pCGR-5 (Δ6) | pCGR-5 (Δ6) | pCGR-7 (Δ12) |
|---|---|---|---|
| 25 μM sub. | 10.3 | 8.7 | 115.7 |
| 25 μM◇ sub. | 29.6 | ND | 39◇ |

◇no glucose in media
sub. is substrate concentration
ND (not done)
*18:1, the substrate, is an endogenous yeast lipid

Example 7

Distribution of PUFAs in Yeast Lipid Fractions

Table 5 illustrates the uptake of free fatty acids and their new products formed in yeast lipids as distributed in the major lipid fractions. A total lipid extract was prepared as described above. The lipid extract was separated on TLC plates, and the fractions were identified by comparison to standards. The bands were collected by scraping, and internal standards were added. The fractions were then saponified and methylated as above, and subjected to gas chromatography. The gas chromatograph calculated the amount of fatty acid by comparison to a standard. The phospholipid fraction contained the highest amount of substrate and product PUFAs for Δ6-desaturase activity. It would appear that the substrates are accessible in the phospholipid form to the desaturases.

TABLE 5

Fatty Acid Distribution in Various Yeast Lipid Fractions in μg

| Fatty acid fraction | Phospholipid | Diglyceride | Free Fatty Acid | Triglyceride | Cholesterol Ester |
|---|---|---|---|---|---|
| SC (pCGR-5) substrate 18:2 | 166.6 | 6.2 | 15 | 18.2 | 15.6 |
| SC (pCGR-5) product γ-18:3 | 61.7 | 1.6 | 4.2 | 5.9 | 1.2 |

SC = *S. cerevisiae (plasmid)*

Example 8

Further Culture Optimization and Coexgression of Δ6 and Δ12-desaturases

This experiment was designed to evaluate the growth and induction conditions for optimal activities of desaturases in *Saccharomyces cerevisiae*. A *Saccharomyces cerevisiae* strain (SC334) capable of producing γ-linolenic acid (GLA) was developed, to assess the feasibility of production of PUFA in yeast. The genes for Δ6 and Δ12-desaturases from *M. alpina* were coexpressed in SC334. Expression of Δ12-desaturase converted oleic acid (present in yeast) to linoleic acid. The linoleic acid was used as a substrate by the Δ6-desaturase to produce GLA. The quantity of GLA produced ranged between 5–8% of the total fatty acids produced in SC334 cultures and the conversion rate of linoleic acid to γ-linolenic acid ranged between 30% to 50%. The induction temperature was optimized, and the effect of changing host strain and upstream promoter sequences on expression of Δ6 and Δ12 (MA 524 and MA 648 respectively) desaturase genes was also determined.

Plasmid Construction

The cloning of pCGR5 as well as pCGR7 has been discussed above. To construct pCGR9a and pCGR9b, the Δ6 and Δ12-desaturase genes were amplified using the following sets of primers. The primers pRDS1 and 3 had Xhol site and primers pRDS2 and 4 had Xbal site (indicated in bold).

I. Δ6-desaturase amplification primers a. pRDS1 tac caa ctc gag aaa atg gct gct gct ccc agt gtg agg (SEQ ID NO:15)

b. pRDS2 aac tga tet aga tta ctg cgc ctt acc cat ctt gga ggc (SEQ ID NO:16)

II. Δ12-desaturase amplification primers a. pRDS3 tac caa ctc gag aaa atg gca cct ccc aac act atc gat (SEQ ID NO:17)

b. pRDS4 aac tga tct aga tta ctt ctt gaa aaa gac cac gtc tcc (SEQ ID NO:18)

The pCGR5 and pCGR7 constructs were used as template DNA for amplification of Δ6 and Δ12-desaturase genes, respectively. The amplified products were digested with Xbal and Xho to create "sticky ends". The PCR amplified Δ6-desaturase with Xhol-Xbal ends as cloned into pCGR7, which was also cut with Xho-1-Xbal. This procedure placed the Δ6-desaturase behind the Δ12-desaturase, under the control of an inducible promoter GAL 1. This construct was designated pCGR9a. Similarly, to construct pCGR9b, the Δ12-desaturase with XhoI-XbaI ends was cloned in the XhoI-Xbal sites of pCGR5. In pCGR9b the Δ12-desaturase was behind the Δ6-desaturase gene, away from the GAL promoter.

To construct pCGR10, the vector pRS425, which contains the constitutive Glyceraldehyde 3-Phosphate Dehydrogenase (GPD) promoter, was digested with BamH1 and pCGR5 was digested with BamH1-Xhol to release the Δ6-desaturase gene. This Δ6-desaturase fragment and BamH1 cut pRS425 were filled using Klenow Polymerase to create blunt ends and ligated, resulting in pCGR10a and pCGR10b containing the Δ6-desaturase gene in the sense and antisense orientation, respectively. To construct pCGR11 and pCGR12, the Δ6 and Δ12-desaturase genes were isolated from pCGR5 and pCGR7, respectively, using an EcoR1-XhoI double digest. The EcoR1-Xhol fragments of Δ6 and Δ12-desaturases were cloned into the pYX242 vector digested with EcoR1-Xhol. The pYX242 vector has the promoter of TP1 (a yeast housekeeping gene), which allows constitutive expression.

Yeast Transformation and Expression

Difference combinations of pCGR5, pCGR7, pCGR9a, pCGR9b, pCGR10a, pCGR11 and pCGR12 were introduced into various host strains of *Saccharomyces cerevisiae*. Transformation was done using PEG/LiAc protocol (Methods in Enzymology Vol. 194 (1991): 186–187). Transformants were selected by plating on synthetic media lacking the appropriate amino acid. The pCGR5, pCGR7, pCGR9a and pCGR9b can be selected on media lacking uracil. The pCGR10, pCGR11 and pCGR12 constructs can be selected on media lacking leucine. Growth of cultures and fatty acid analysis was performed as in Example 5 above.

Production of GLA

Production of GLA requires the expression of two enzymes (the Δ6 and Δ12-desaturases), which are absent in yeast. To express these enzymes at optimum levels the following constructs or combinations of constructs, were introduced into various host strains:

1) pCGR9a/SC334
2) pCGR9b/SC334
3) pCGR10a and pCGR7/SC334
4) pCGR11 and pCGR7/SC334
5) pCGR12 and pCGR5/SC334
6) pCGR10a and pCGR7/DBY746
7) pCGR10a and pCGR7/DBY746

Figure 6B:
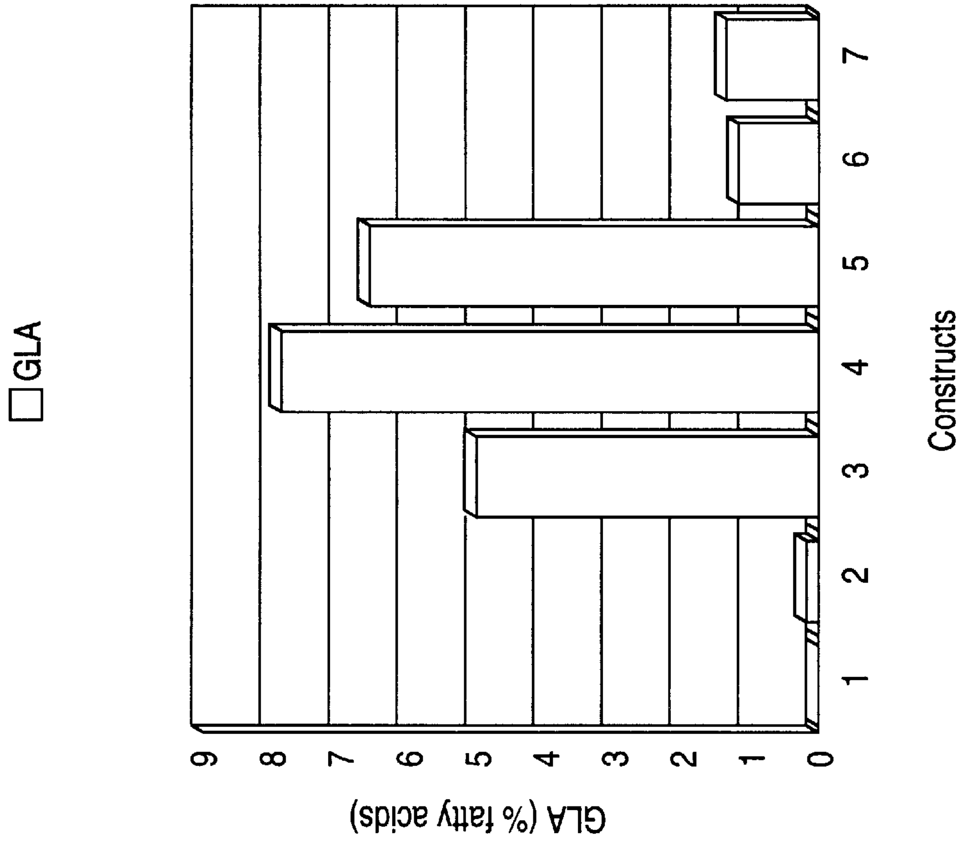
FIGS. 6A and 6B show the effect of different expression constructs on expression of GLA in yeast.
Figure 6A:
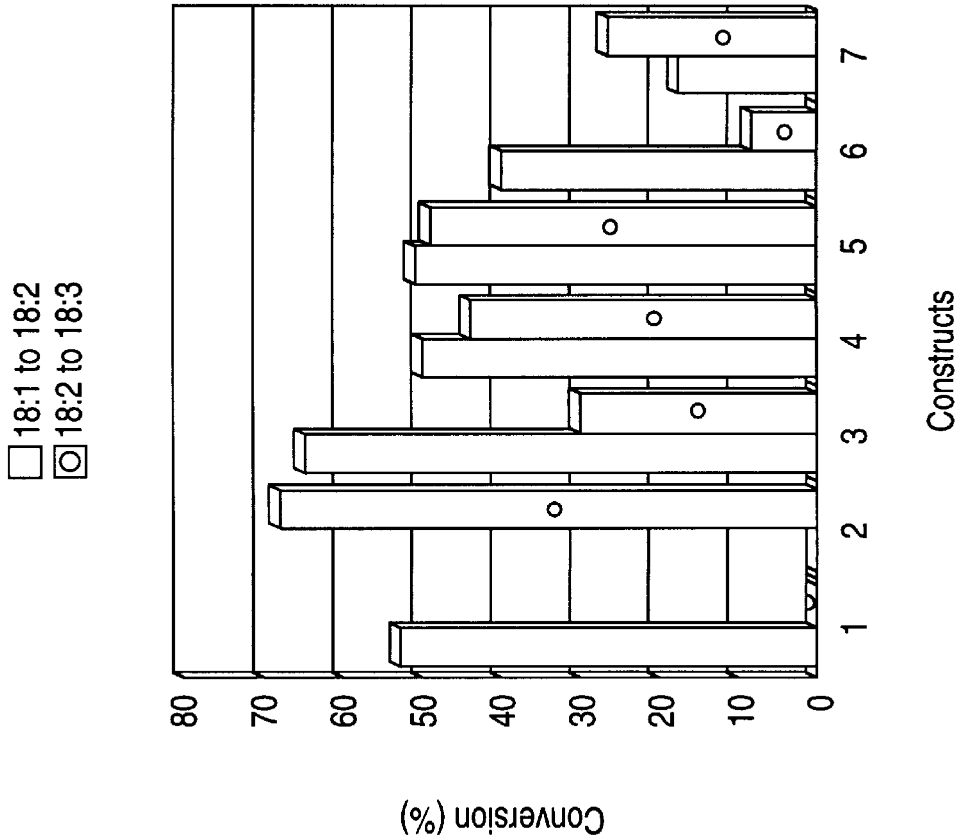

The pCGR9a construct has both the Δ6 and Δ12-desaturase genes under the control of an inducible GAL promoter. The SC334 host cells transformed with this construct did not show any GLA accumulation in total fatty acids (FIG. 6A and B, lane 1). However, when the Δ6 and Δ12-desaturase genes were individually controlled by the GAL promoter, the control constructs were able to express Δ6 and Δ12-desaturase, as evidenced by the conversion of their respective substrates to products. The Δ12-desaturase gene in pCGR9a was expressed as evidenced by the conversion of 18:1n-9 to 18:2n-6 in pCGR9a/SC334, while the Δ6-desaturase gene was not expressed/active, because the 18:2n-6 was not being converted to 18:3n-6 (FIG. 6A and B, lane 1).

The pCGR9b construct also had both the Δ6 and Δ12-desaturase genes under the control of the GAL promoter but in an inverse order compared to pCGR9a. In this case, very little GLA (<1%) was seen in pCGR9b/SC334 cultures. The expression of Δ12 was also very low, as evidenced by the low percentage of 18:2 in the total fatty acids (FIG. 6A and B, lane 1).

To test if expressing both enzymes under the control of independent promoters would increase GLA production, the Δ6-desaturase gene was cloned into the pRS425 vector. The construct of pCGR10a has the Δ6-desaturase in the correct orientation, under control of constitutive GPD promoter. The pCGR10b has the Δ6-desaturase gene in the inverse orientation, and serves as the negative control. The pCGR10a/SC334cells produced significantly higher levels of GLA (5% of the total fatty acids, FIG. 6, lane 3), compared to pCGR9a. Both the Δ6 and Δ12-desaturase genes were expressed at high level because the conversion of 18:1→18:2 was 65%, while the conversion of 18:2→18:3 (Δ6-desaturase) was 30% (FIG. 6, lane 3). As expected, the negative control pCGR10b/SC334 did not show any GLA.

To further optimize GLA production, the Δ6 and Δ12 genes were introduced into the PYX242 vector, creating pCGR11 and pCGR12 respectively. The PYX242 vector allows for constitutive expression by the TP1 promoter (Alber, T. and Kawasaki, G. (1982). *J Mol & Appl. Genetics* 1:419). The introduction of pCGR11 and pCGR7/SC334 gene resulted in approximately 8% of GLA in total fatty acids of SC334. The rate of conversion of 18:1→18:2 and 18:2→18:3 was approximately 50% and 44% respectively (FIG. 6A and B, lane 4). The presence of pCGR12 and pCGR5 in SC334 resulted in 6.6% GLA in total fatty acids with a conversion rate of approximately 50% for both 18:1 to 18:2 and 18:2 to 18:3, respectively (FIG. 6A and B, lane 5). Thus although the quantity of GLA in total fatty acids was higher in the pCGR11/pCGR7 combination of constructs, the conversion rates of substrate to product were better for the pCGR12/pCGR5 combination.

Figure 7A:
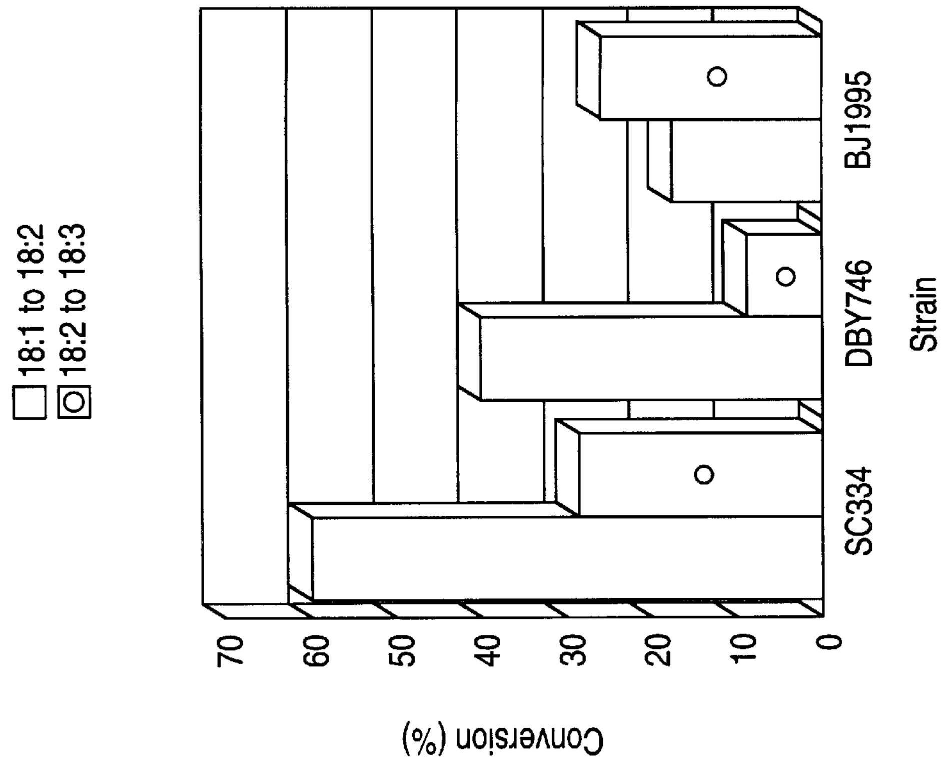
FIGS. 7A and 7B show the effect of host strain on GLA production.
Figure 7B:
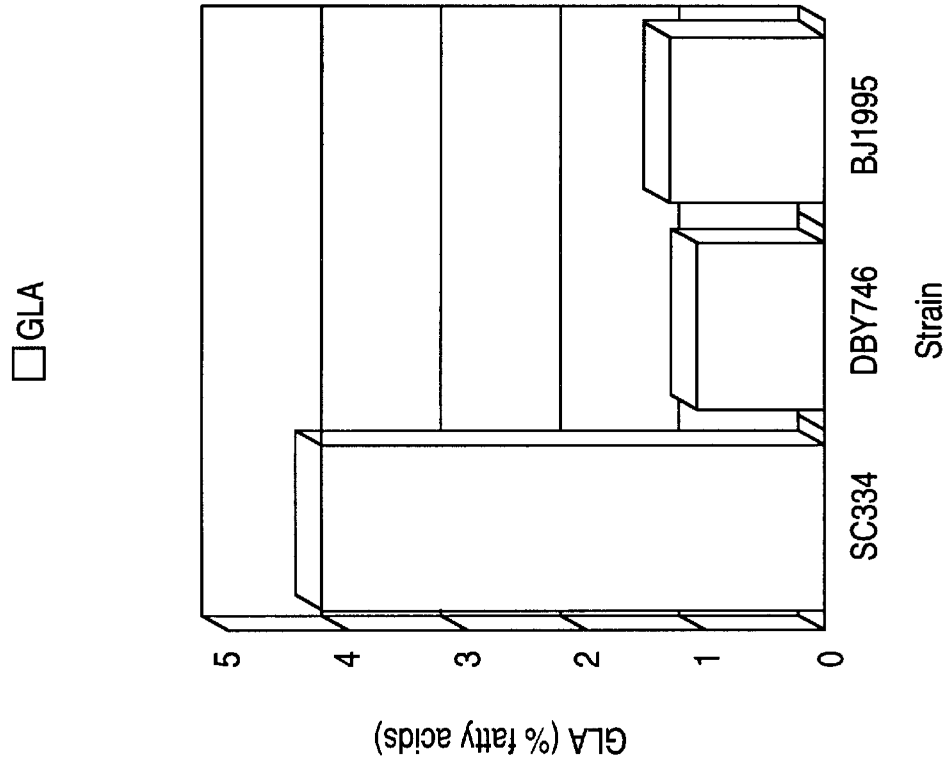

To determine if changing host strain would increase GLA production, pCGR10a and pCGR7 were introduced into the host strain BJ1995 and DBY746 (obtained from the Yeast Genetic Stock Centre, 1021 Donner Laboratory, Berkeley, Calif. 94720. The genotype of strain DBY746 is Matα, his3-Δ1, leu2-3, leu2-112, ura3-32, trpl-289, gal). The results are shown in FIG. 7. Changing host strain to BJ1995 did not improve the GLA production, because the quantity of GLA was only 1.31% of total fatty acids and the conversion rate of 18:1→18:2 was approximately 17% in BJ1995. No GLA was observed in DBY746 and the conversion of 18:1→18:2 was very low (<1% in control) suggesting that a cofactor required for the expression of Δ12-desaturase might be missing in DB746 (FIG. 7, lane 2).

Figure 8B:
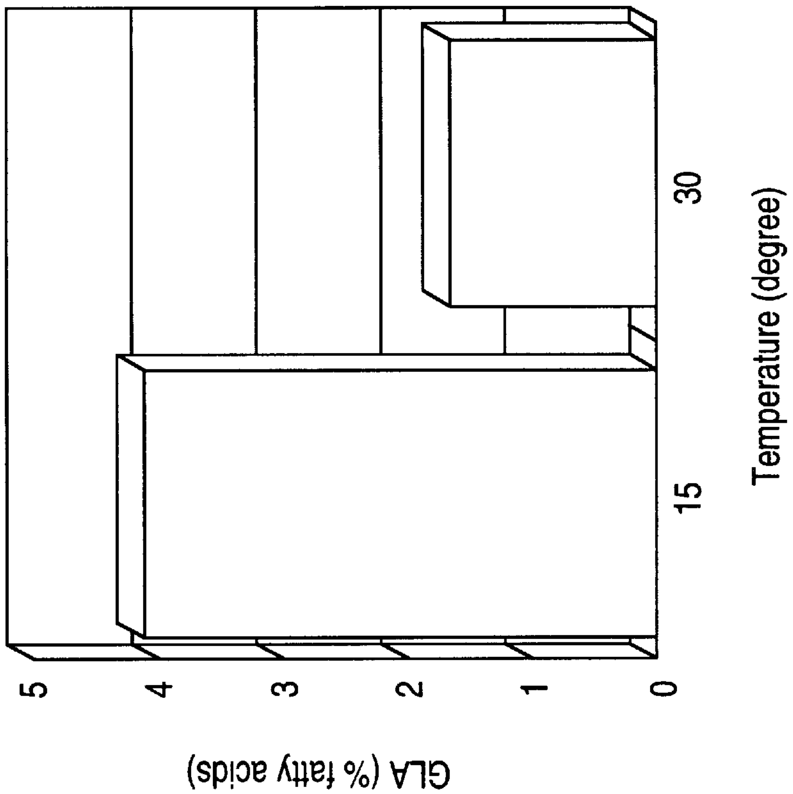
FIGS. 8A and 8B show the effect of temperature on GLA production in *S. cerevisiae* strain SC334.
Figure 8A:
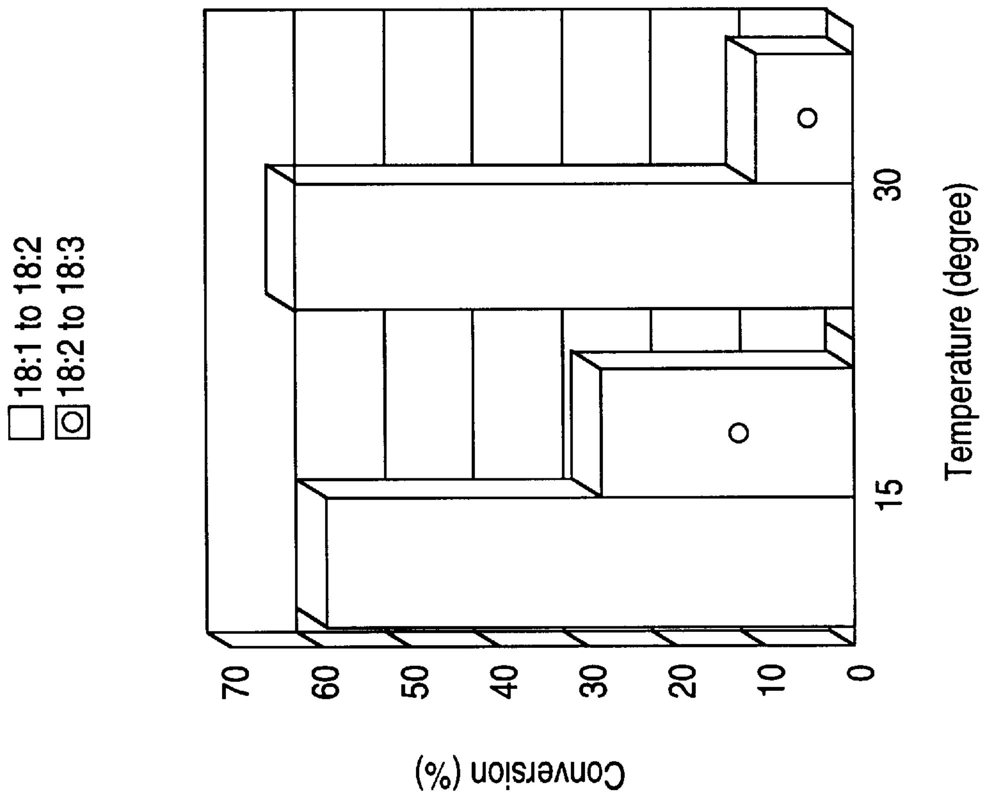

To determine the effect of temperature on GLA production, pCGR10a and pCGR7/SC334 cultures were grown at 15° C. and 30° C. Higher levels of GLA were found in cultures grown and induced at 15° C. than those in cultures grown at 30° C. (4.23% vs. 1.68%). This was due to a lower conversion rate of 18:2→18:3 at 30° C. (11.6% vs. 29% in 15° C.) cultures, despite a higher conversion of 18:1→18:2 (65% vs. 60% at 30° C. (FIG. 8). These results suggest that Δ12 and Δ6 may have different optimal expression temperatures.

Of the various parameters examined in this study, temperature of growth, yeast host strain and media components had the most significant impact on the expression of desaturase, while timing of substrate addition and concentration of inducer did not significantly affect desaturase expression.

These data show that two DNAs encoding desaturases that can convert LA to GLA or oleic acid to LA can be isolated from *Mortierella alpina* and can be expressed, either individually or in combination, in a heterologous system and used to produce poly-unsaturated long chain fatty acids. Exemplified is the production of GLA from oleic acid by expression of Δ12- and Δ6-desaturases in yeast.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated nucleic acid comprising a nucleotide sequence which encodes a polypeptide from *Mortierella alpina* having desaturase activity that desaturates a fatty acid molecule at carbon 6 or 12.

2. An isolated nucleic acid encoding a polypeptide having an amino acid sequence depicted in SEQ ID NO: 2 or SEQ ID NO: 4.

3. An isolated nucleic acid comprising the nucleotide sequence depicted in a SEQ ID NO: 1 or SEQ ID NO:3.

4. A nucleic acid fragment consisting of: at least 50 contiguous nucleotides of the sequences depicted in SEQ ID NO: 1 or SEQ ID NO: 3 or their complementary sequences.

5. A nucleic acid construct comprising the nucleotide sequence of claim 1 operably associated with an expression control sequence functional in a microbial cell.

6. The nucleic acid construct according to claim 5, wherein said microbial cell is a yeast cell.

7. The host cell of claim 5 wherein said expression control sequence is exogenously supplied to said microbial cell.

8. A nucleic acid construct comprising the nucleotide sequence depicted in SEQ ID NO: 1 or SEQ ID NO: 3 linked to a heterologous nucleic acid.

9. A nucleic acid construct comprising a nucleotide sequence which encodes a polypeptide comprising an amino acid sequence depicted in SEQ ID NO: 2 or SEQ ID NO: 4.

10. The nucleic acid construct according to claim 9 wherein said amino acid sequence comprises amino acids 1 through 457 of the sequence depicted in SEQ ID NO: 2.

11. A nucleic acid construct comprising a fungal nucleotide sequence which encodes a functionally active protein having desaturase activity that desaturates a fatty acid molecule at carbon 12 said protein having an amino acid sequence depicted in a SEQ ID NO: 4.

12. A recombinant yeast cell comprising a nucleic acid construct according to claim 11.

13. The recombinant yeast cell according to claim 12, wherein said yeast cell is a Saaccharomyces cell.

14. A host cell comprising a nucleic acid construct according to claims 9 or 11.

15. A recombinant yeast cell comprising at least one copy of a vector comprising a *Mortierella alpina* nucleotide sequence which encodes a polypeptide having desaturase activity that desaturates a fatty acid molecule at carbon 6 or 12 wherein said yeast cell or an ancestor of said yeast cell was transformed with said vector to produce said recombinant yeast cell, and wherein said nucleotide sequence is operably associated with an expression control sequence functional in said recombinant yeast cell.

16. The recombinant yeast cell according to claim 15 wherein said recombinant yeast cell is a Saccharomyces cell.

17. The yeast cell according to claim 15, wherein said expression control sequence is provided in said expression vector.

18. A host cell comprising a vector which includes a nucleic acid which encodes a fatty acid desaturase derived from *Mortierella alpina*, wherein said desaturase has an amino acid sequence represented by SEQ ID NO: 2 or SEQ ID NO: 4, and wherein said nucleic acid is operably linked to a promoter.

19. The host cell according to claim 18, wherein said host cell is a eukaryotic cell.

20. The host cell according to claim 19, wherein said eukaryotic cell is selected from the group consisting of a mammalian cell, a plant cell, an insect cell, a fungal cell, an avian cell and an algal cell.

21. The host cell according to claim 19, wherein said host cell contains dihomo-gamma-linolenic acid.

22. An isolated nucleic acid from *Mortierella alpina* encoding a polypeptide having desaturase activity that desaturates a fatty acid molecule at carbon 6 or 12.

23. A nucleic acid construct comprising the nucleic acid of claim 22.

24. The nucleic acid construct of claim 23 wherein said nucleic acid is operably associated with an expression control sequence functional in a microbial cell.

25. The nucleic acid construct of claim 24 wherein said microbial cell is a yeast cell.

26. A host cell comprising the nucleic acid construct of claim 23.

27. The host cell according to claim 26, wherein said host cell is a eukaryotic cell.

28. The host cell according to claim 27, wherein said eukaryotic cell is selected from the group consisting of a mammalian cell, a plant cell, an insect cell, a fungal cell, an avian cell and an algal cell.

29. The host cell according to claim 27, wherein said host cell contains dihomo-gamma-linolenic acid.

30. A recombinant yeast cell comprising at least one nucleic acid construct comprising a nucleotide sequence which encodes a functionally active protein having desaturase activity that desaturates a fatty acid molecule at carbon 6, said protein having an amino acid sequence depicted in SEQ ID NO: 2, and at least one nucleic acid construct comprising a nucleic acid sequence which encodes a functionally active protein having desaturase activity that desaturates a fatty acid molecule at carbon 12, said protein having an amino acid sequence depicted in SEQ ID NO: 4, wherein said nucleic acid constructs are operably associated with transcription control sequences functional in a yeast cell.

* * * * *

UNITED STATES PATENT AND TRADEMARK OFFICE

CERTIFICATE OF CORRECTION

PATENT NO. : 5,968,809
DATED : October 19, 1999
INVENTOR(S) : DEBORAH KNUTZON ET AL.

It is certified that error appears in the above-identified patent and that said Letters Patent is hereby corrected as shown below:

On the Title page, item [73] Assignee:

please change "Abbot" to --Abbott--;

In Col. 6, line 2, please change "Saccharomyces" to --*Saccharomyces*--;

In Col. 6, line 5, please insert --18:1 fatty acids to 18:2 fatty acids, 18:2 fatty acids to 18:3 fatty acids and/or 18:3 fatty acids to 18:4 fatty acids-- after "converts";

In Col. 21, line 3, please change "manufactur's" to --manufacturer's--;

In Col. 51, line 38, please change "Saaccharomyces" to --*Saccharomyces*--;
In Col. 51, line 51, please change "Saccharomyces" to --*Saccharomyces*--.

Signed and Sealed this

Eighth Day of August, 2000

*Attest:*

Q. TODD DICKINSON

*Attesting Officer*

*Director of Patents and Trademarks*

SEQUENCE LISTING

```
(1) GENERAL INFORMATION:

   (iii) NUMBER OF SEQUENCES: 18


(2) INFORMATION FOR SEQ ID NO:1:

     (i) SEQUENCE CHARACTERISTICS:
          (A) LENGTH: 1617 base pairs
          (B) TYPE: nucleic acid
          (C) STRANDEDNESS: single
          (D) TOPOLOGY: linear

    (ii) MOLECULE TYPE: other nucleic acid

    (xi) SEQUENCE DESCRIPTION: SEQ ID NO:1:

CGACACTCCT TCCTTCTTCT CACCCGTCCT AGTCCCCTTC AACCCCCCTC TTTGACAAAG     60

ACAACAAACC ATGGCTGCTG CTCCCAGTGT GAGGACGTTT ACTCGGGCCG AGGTTTTGAA    120

TGCCGAGGCT CTGAATGAGG GCAAGAAGGA TGCCGAGGCA CCCTTCTTGA TGATCATCGA    180

CAACAAGGTG TACGATGTCC GCGAGTTCGT CCCTGATCAT CCCGGTGGAA GTGTGATTCT    240

CACGCACGTT GGCAAGGACG GCACTGACGT CTTTGACACT TTTCACCCCG AGGCTGCTTG    300

GGAGACTCTT GCCAACTTTT ACGTTGGTGA TATTGACGAG AGCGACCGCG ATATCAAGAA    360

TGATGACTTT GCGGCCGAGG TCCGCAAGCT GCGTACCTTG TTCCAGTCTC TTGGTTACTA    420

CGATTCTTCC AAGGCATACT ACGCCTTCAA GGTCTCGTTC AACCTCTGCA TCTGGGGTTT    480

GTCGACGGTC ATTGTGGCCA AGTGGGGCCA GACCTCGACC CTCGCCAACG TGCTCTCGGC    540

TGCGCTTTTG GGTCTGTTCT GGCAGCAGTG CGGATGGTTG GCTCACGACT TTTTGCATCA    600

CCAGGTCTTC CAGGACCGTT TCTGGGGTGA TCTTTTCGGC GCCTTCTTGG GAGGTGTCTG    660

CCAGGGCTTC TCGTCCTCGT GGTGGAAGGA CAAGCACAAC ACTCACCACG CCGCCCCCAA    720
```

-continued

```
CGTCCACGGC GAGGATCCCG ACATTGACAC CCACCCTCTG TTGACCTGGA GTGAGCATGC     780

GTTGGAGATG TTCTCGGATG TCCCAGATGA GGAGCTGACC CGCATGTGGT CGCGTTTCAT     840

GGTCCTGAAC CAGACCTGGT TTTACTTCCC CATTCTCTCG TTTGCCCGTC TCTCCTGGTG     900

CCTCCAGTCC ATTCTCTTTG TGCTGCCTAA CGGTCAGGCC CACAAGCCCT CGGGCGCGCG     960

TGTGCCCATC TCGTTGGTCG AGCAGCTGTC GCTTGCGATG CACTGGACCT GGTACCTCGC    1020

CACCATGTTC CTGTTCATCA AGGATCCCGT CAACATGCTG GTGTACTTTT TGGTGTCGCA    1080

GGCGGTGTGC GGAAACTTGT TGGCGATCGT GTTCTCGCTC AACCACAACG GTATGCCTGT    1140

GATCTCGAAG GAGGAGGCGG TCGATATGGA TTTCTTCACG AAGCAGATCA TCACGGGTCG    1200

TGATGTCCAC CCGGGTCTAT TTGCCAACTG GTTCACGGGT GGATTGAACT ATCAGATCGA    1260

GCACCACTTG TTCCCTTCGA TGCCTCGCCA CAACTTTTCA AAGATCCAGC CTGCTGTCGA    1320

GACCCTGTGC AAAAAGTACA ATGTCCGATA CCACACCACC GGTATGATCG AGGGAACTGC    1380

AGAGGTCTTT AGCCGTCTGA ACGAGGTCTC CAAGGCTGCC TCCAAGATGG GTAAGGCGCA    1440

GTAAAAAAAA AAACAAGGAC GTTTTTTTTC GCCAGTGCCT GTGCCTGTGC CTGCTTCCCT    1500

TGTCAAGTCG AGCGTTTCTG GAAAGGATCG TTCAGTGCAG TATCATCATT CTCCTTTTAC    1560

CCCCCGCTCA TATCTCATTC ATTTCTCTTA TTAAACAACT TGTTCCCCCC TTCACCG       1617
```

(2) INFORMATION FOR SEQ ID NO:2:

(i) SEQUENCE CHARACTERISTICS:
(A) LENGTH: 457 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:2:

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190
```

```
Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455
```

(2) INFORMATION FOR SEQ ID NO:3:

(i) SEQUENCE CHARACTERISTICS:
(A) LENGTH: 1488 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

```
GTCCCCTGTC GCTGTCGGCA CACCCCATCC TCCCTCGCTC CCTCTGCGTT TGTCCTTGGC     60

CCACCGTCTC TCCTCCACCC TCCGAGACGA CTGCAACTGT AATCAGGAAC CGACAAATAC    120

ACGATTTCTT TTTACTCAGC ACCAACTCAA AATCCTCAAC CGCAACCCTT TTTCAGGATG    180

GCACCTCCCA ACACTATCGA TGCCGGTTTG ACCCAGCGTC ATATCAGCAC CTCGGCCCCA    240

AACTCGGCCA AGCCTGCCTT CGAGCGCAAC TACCAGCTCC CCGAGTTCAC CATCAAGGAG    300

ATCCGAGAGT GCATCCCTGC CCACTGCTTT GAGCGCTCCG GTCTCCGTGG TCTCTGCCAC    360

GTTGCCATCG ATCTGACTTG GGCGTCGCTC TTGTTCCTGG CTGCGACCCA GATCGACAAG    420

TTTGAGAATC CCTTGATCCG CTATTTGGCC TGGCCTGTTT ACTGGATCAT GCAGGGTATT    480
```

-continued

```
GTCTGCACCG GTGTCTGGGT GCTGGCTCAC GAGTGTGGTC ATCAGTCCTT CTCGACCTCC    540

AAGACCCTCA ACAACACAGT TGGTTGGATC TTGCACTCGA TGCTCTTGGT CCCCTACCAC    600

TCCTGGAGAA TCTCGCACTC GAAGCACCAC AAGGCCACTG GCCATATGAC CAAGGACCAG    660

GTCTTTGTGC CCAAGACCCG CTCCCAGGTT GGCTTGCCTC CCAAGGAGAA CGCTGCTGCT    720

GCCGTTCAGG AGGAGGACAT GTCCGTGCAC CTGGATGAGG AGGCTCCCAT TGTGACTTTG    780

TTCTGGATGG TGATCCAGTT CTTGTTCGGA TGGCCCGCGT ACCTGATTAT GAACGCCTCT    840

GGCCAAGACT ACGGCCGCTG GACCTCGCAC TTCCACACGT ACTCGCCCAT CTTTGAGCCC    900

CGCAACTTTT TCGACATTAT TATCTCGGAC CTCGGTGTGT TGGCTGCCCT CGGTGCCCTG    960

ATCTATGCCT CCATGCAGTT GTCGCTCTTG ACCGTCACCA AGTACTATAT TGTCCCCTAC   1020

CTCTTTGTCA ACTTTTGGTT GGTCCTGATC ACCTTCTTGC AGCACACCGA TCCCAAGCTG   1080

CCCCATTACC GCGAGGGTGC CTGGAATTTC CAGCGTGGAG CTCTTTGCAC CGTTGACCGC   1140

TCGTTTGGCA AGTTCTTGGA CCATATGTTC CACGGCATTG TCCACACCCA TGTGGCCCAT   1200

CACTTGTTCT CGCAAATGCC GTTCTACCAT GCTGAGGAAG CTACCTATCA TCTCAAGAAA   1260

CTGCTGGGAG AGTACTATGT GTACGACCCA TCCCCGATCG TCGTTGCGGT CTGGAGGTCG   1320

TTCCGTGAGT GCCGATTCGT GGAGGATCAG GGAGACGTGG TCTTTTTCAA GAAGTAAAAA   1380

AAAAGACAAT GGACCACACA CAACCTTGTC TCTACAGACC TACGTATCAT GTAGCCATAC   1440

CACTTCATAA AAGAACATGA GCTCTAGAGG CGTGTCATTC GCGCCTCC                1488
```

(2) INFORMATION FOR SEQ ID NO:4:

(i) SEQUENCE CHARACTERISTICS:
(A) LENGTH: 399 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:4:

```
Met Ala Pro Pro Asn Thr Ile Asp Ala Gly Leu Thr Gln Arg His Ile
1               5                   10                  15

Ser Thr Ser Ala Pro Asn Ser Ala Lys Pro Ala Phe Glu Arg Asn Tyr
            20                  25                  30

Gln Leu Pro Glu Phe Thr Ile Lys Glu Ile Arg Glu Cys Ile Pro Ala
        35                  40                  45

His Cys Phe Glu Arg Ser Gly Leu Arg Gly Leu Cys His Val Ala Ile
    50                  55                  60

Asp Leu Thr Trp Ala Ser Leu Leu Phe Leu Ala Ala Thr Gln Ile Asp
65                  70                  75                  80

Lys Phe Glu Asn Pro Leu Ile Arg Tyr Leu Ala Trp Pro Val Tyr Trp
                85                  90                  95

Ile Met Gln Gly Ile Val Cys Thr Gly Val Trp Val Leu Ala His Glu
            100                 105                 110

Cys Gly His Gln Ser Phe Ser Thr Ser Lys Thr Leu Asn Asn Thr Val
        115                 120                 125

Gly Trp Ile Leu His Ser Met Leu Leu Val Pro Tyr His Ser Trp Arg
    130                 135                 140

Ile Ser His Ser Lys His His Lys Ala Thr Gly His Met Thr Lys Asp
145                 150                 155                 160

Gln Val Phe Val Pro Lys Thr Arg Ser Gln Val Gly Leu Pro Pro Lys
                165                 170                 175
```

-continued

```
Glu Asn Ala Ala Ala Ala Val Gln Glu Glu Asp Met Ser Val His Leu
            180                 185                 190

Asp Glu Glu Ala Pro Ile Val Thr Leu Phe Trp Met Val Ile Gln Phe
        195                 200                 205

Leu Phe Gly Trp Pro Ala Tyr Leu Ile Met Asn Ala Ser Gly Gln Asp
    210                 215                 220

Tyr Gly Arg Trp Thr Ser His Phe His Thr Tyr Ser Pro Ile Phe Glu
225                 230                 235                 240

Pro Arg Asn Phe Phe Asp Ile Ile Ile Ser Asp Leu Gly Val Leu Ala
                245                 250                 255

Ala Leu Gly Ala Leu Ile Tyr Ala Ser Met Gln Leu Ser Leu Leu Thr
            260                 265                 270

Val Thr Lys Tyr Tyr Ile Val Pro Tyr Leu Phe Val Asn Phe Trp Leu
        275                 280                 285

Val Leu Ile Thr Phe Leu Gln His Thr Asp Pro Lys Leu Pro His Tyr
    290                 295                 300

Arg Glu Gly Ala Trp Asn Phe Gln Arg Gly Ala Leu Cys Thr Val Asp
305                 310                 315                 320

Arg Ser Phe Gly Lys Phe Leu Asp His Met Phe His Gly Ile Val His
                325                 330                 335

Thr His Val Ala His His Leu Phe Ser Gln Met Pro Phe Tyr His Ala
            340                 345                 350

Glu Glu Ala Thr Tyr His Leu Lys Lys Leu Leu Gly Glu Tyr Tyr Val
        355                 360                 365

Tyr Asp Pro Ser Pro Ile Val Val Ala Val Trp Arg Ser Phe Arg Glu
    370                 375                 380

Cys Arg Phe Val Glu Asp Gln Gly Asp Val Val Phe Phe Lys Lys
385                 390                 395
```

(2) INFORMATION FOR SEQ ID NO:5:

(i) SEQUENCE CHARACTERISTICS:
(A) LENGTH: 355 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:5:

```
Glu Val Arg Lys Leu Arg Thr Leu Phe Gln Ser Leu Gly Tyr Tyr Asp
1               5                   10                  15

Ser Ser Lys Ala Tyr Tyr Ala Phe Lys Val Ser Phe Asn Leu Cys Ile
            20                  25                  30

Trp Gly Leu Ser Thr Val Ile Val Ala Lys Trp Gly Gln Thr Ser Thr
        35                  40                  45

Leu Ala Asn Val Leu Ser Ala Ala Leu Leu Gly Leu Phe Trp Gln Gln
    50                  55                  60

Cys Gly Trp Leu Ala His Asp Phe Leu His His Gln Val Phe Gln Asp
65                  70                  75                  80

Arg Phe Trp Gly Asp Leu Phe Gly Ala Phe Leu Gly Gly Val Cys Gln
                85                  90                  95

Gly Phe Ser Ser Ser Trp Trp Lys Asp Lys His Asn Thr His His Ala
            100                 105                 110

Ala Pro Asn Val His Gly Glu Asp Pro Asp Ile Asp Thr His Pro Leu
        115                 120                 125
```

-continued

```
Leu Thr Trp Ser Glu His Ala Leu Glu Met Phe Ser Asp Val Pro Asp
    130                 135                 140

Glu Glu Leu Thr Arg Met Trp Ser Arg Phe Met Val Leu Asn Gln Thr
145                 150                 155                 160

Trp Phe Tyr Phe Pro Ile Leu Ser Phe Ala Arg Leu Ser Trp Cys Leu
                165                 170                 175

Gln Ser Ile Leu Phe Val Leu Pro Asn Gly Gln Ala His Lys Pro Ser
            180                 185                 190

Gly Ala Arg Val Pro Ile Ser Leu Val Glu Gln Leu Ser Leu Ala Met
        195                 200                 205

His Trp Thr Trp Tyr Leu Ala Thr Met Phe Leu Phe Ile Lys Asp Pro
    210                 215                 220

Val Asn Met Leu Val Tyr Phe Leu Val Ser Gln Ala Val Cys Gly Asn
225                 230                 235                 240

Leu Leu Ala Ile Val Phe Ser Leu Asn His Asn Gly Met Pro Val Ile
                245                 250                 255

Ser Lys Glu Glu Ala Val Asp Met Asp Phe Phe Thr Lys Gln Ile Ile
            260                 265                 270

Thr Gly Arg Asp Val His Pro Gly Leu Phe Ala Asn Trp Phe Thr Gly
        275                 280                 285

Gly Leu Asn Tyr Gln Ile Glu His His Leu Phe Pro Ser Met Pro Arg
    290                 295                 300

His Asn Phe Ser Lys Ile Gln Pro Ala Val Glu Thr Leu Cys Lys Lys
305                 310                 315                 320

Tyr Asn Val Arg Tyr His Thr Thr Gly Met Ile Glu Gly Thr Ala Glu
                325                 330                 335

Val Phe Ser Arg Leu Asn Glu Val Ser Lys Ala Ala Ser Lys Met Gly
            340                 345                 350

Lys Ala Gln
        355
```

(2) INFORMATION FOR SEQ ID NO:6:

(i) SEQUENCE CHARACTERISTICS:
(A) LENGTH: 104 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:6:

```
Val Thr Leu Tyr Thr Leu Ala Phe Val Ala Ala Asn Ser Leu Gly Val
1               5                   10                  15

Leu Tyr Gly Val Leu Ala Cys Pro Ser Val Xaa Pro His Gln Ile Ala
            20                  25                  30

Ala Gly Leu Leu Gly Leu Leu Trp Ile Gln Ser Ala Tyr Ile Gly Xaa
        35                  40                  45

Asp Ser Gly His Tyr Val Ile Met Ser Asn Lys Ser Asn Asn Xaa Phe
    50                  55                  60

Ala Gln Leu Leu Ser Gly Asn Cys Leu Thr Gly Ile Ile Ala Trp Trp
65                  70                  75                  80

Lys Trp Thr His Asn Ala His His Leu Ala Cys Asn Ser Leu Asp Tyr
                85                  90                  95

Gly Pro Asn Leu Gln His Ile Pro
            100
```

(2) INFORMATION FOR SEQ ID NO:7:

(i) SEQUENCE CHARACTERISTICS:
(A) LENGTH: 252 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:7:

```
Gly Val Leu Tyr Gly Val Leu Ala Cys Thr Ser Val Phe Ala His Gln
1               5                   10                  15

Ile Ala Ala Ala Leu Leu Gly Leu Leu Trp Ile Gln Ser Ala Tyr Ile
            20                  25                  30

Gly His Asp Ser Gly His Tyr Val Ile Met Ser Asn Lys Ser Tyr Asn
        35                  40                  45

Arg Phe Ala Gln Leu Leu Ser Gly Asn Cys Leu Thr Gly Ile Ser Ile
    50                  55                  60

Ala Trp Trp Lys Trp Thr His Asn Ala His His Leu Ala Cys Asn Ser
65                  70                  75                  80

Leu Asp Tyr Asp Pro Asp Leu Gln His Ile Pro Val Phe Ala Val Ser
                85                  90                  95

Thr Lys Phe Phe Ser Ser Leu Thr Ser Arg Phe Tyr Asp Arg Lys Leu
            100                 105                 110

Thr Phe Gly Pro Val Ala Arg Phe Leu Val Ser Tyr Gln His Phe Thr
        115                 120                 125

Tyr Tyr Pro Val Asn Cys Phe Gly Arg Ile Asn Leu Phe Ile Gln Thr
    130                 135                 140

Phe Leu Leu Leu Phe Ser Lys Arg Glu Val Pro Asp Arg Ala Leu Asn
145                 150                 155                 160

Phe Ala Gly Ile Leu Val Phe Trp Thr Trp Phe Pro Leu Leu Val Ser
                165                 170                 175

Cys Leu Pro Asn Trp Pro Glu Arg Phe Phe Phe Val Phe Thr Ser Phe
            180                 185                 190

Thr Val Thr Ala Leu Gln His Ile Gln Phe Thr Leu Asn His Phe Ala
        195                 200                 205

Ala Asp Val Tyr Val Gly Pro Pro Thr Gly Ser Asp Trp Phe Glu Lys
    210                 215                 220

Gln Ala Ala Gly Thr Ile Asp Ile Ser Cys Arg Ser Tyr Met Asp Trp
225                 230                 235                 240

Phe Phe Gly Gly Leu Gln Phe Gln Leu Glu His His
                245                 250
```

(2) INFORMATION FOR SEQ ID NO:8:

(i) SEQUENCE CHARACTERISTICS:
(A) LENGTH: 125 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:8:

```
Gly Xaa Xaa Asn Phe Ala Gly Ile Leu Val Phe Trp Thr Trp Phe Pro
1               5                   10                  15

Leu Leu Val Ser Cys Leu Pro Asn Trp Pro Glu Arg Phe Xaa Phe Val
            20                  25                  30
```

-continued

```
Phe Thr Gly Phe Thr Val Thr Ala Leu Gln His Ile Gln Phe Thr Leu
        35                  40                  45

Asn His Phe Ala Ala Asp Val Tyr Val Gly Pro Pro Thr Gly Ser Asp
    50                  55                  60

Trp Phe Glu Lys Gln Ala Ala Gly Thr Ile Asp Ile Ser Cys Arg Ser
65                  70                  75                  80

Tyr Met Asp Trp Phe Phe Cys Gly Leu Gln Phe Gln Leu Glu His His
                85                  90                  95

Leu Phe Pro Arg Leu Pro Arg Cys His Leu Arg Lys Val Ser Pro Val
            100                 105                 110

Gly Gln Arg Gly Phe Gln Arg Lys Xaa Asn Leu Ser Xaa
        115                 120                 125
```

(2) INFORMATION FOR SEQ ID NO:9:

(i) SEQUENCE CHARACTERISTICS:
(A) LENGTH: 131 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:9:

```
Pro Ala Thr Glu Val Gly Gly Leu Ala Trp Met Ile Thr Phe Tyr Val
1               5                   10                  15

Arg Phe Phe Leu Thr Tyr Val Pro Leu Leu Gly Leu Lys Ala Phe Leu
            20                  25                  30

Gly Leu Phe Phe Ile Val Arg Phe Leu Glu Ser Asn Trp Phe Val Trp
        35                  40                  45

Val Thr Gln Met Asn His Ile Pro Met His Ile Asp His Asp Arg Asn
    50                  55                  60

Met Asp Trp Val Ser Thr Gln Leu Gln Ala Thr Cys Asn Val His Lys
65                  70                  75                  80

Ser Ala Phe Asn Asp Trp Phe Ser Gly His Leu Asn Phe Gln Ile Glu
                85                  90                  95

His His Leu Phe Pro Thr Met Pro Arg His Asn Tyr His Xaa Val Ala
            100                 105                 110

Pro Leu Val Gln Ser Leu Cys Ala Lys His Gly Ile Glu Tyr Gln Ser
        115                 120                 125

Lys Pro Leu
    130
```

(2) INFORMATION FOR SEQ ID NO:10:

(i) SEQUENCE CHARACTERISTICS:
(A) LENGTH: 87 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:10:

```
Cys Ser Pro Lys Ser Ser Pro Thr Arg Asn Met Thr Pro Ser Pro Phe
1               5                   10                  15

Ile Asp Trp Leu Trp Gly Gly Leu Asn Tyr Gln Ile Glu His His Leu
            20                  25                  30
```

-continued

```
Phe Pro Thr Met Pro Arg Cys Asn Leu Asn Arg Cys Met Lys Tyr Val
        35                  40                  45

Lys Glu Trp Cys Ala Glu Asn Asn Leu Pro Tyr Leu Val Asp Asp Tyr
    50                  55                  60

Phe Val Gly Tyr Asn Leu Asn Leu Gln Gln Leu Lys Asn Met Ala Glu
65                  70                  75                  80

Leu Val Gln Ala Lys Ala Ala
                85
```

(2) INFORMATION FOR SEQ ID NO:11:

(i) SEQUENCE CHARACTERISTICS:
(A) LENGTH: 143 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:11:

```
Arg His Glu Ala Ala Arg Gly Gly Thr Arg Leu Ala Tyr Met Leu Val
1               5                   10                  15

Cys Met Gln Trp Thr Asp Leu Leu Trp Ala Ala Ser Phe Tyr Ser Arg
            20                  25                  30

Phe Phe Leu Ser Tyr Ser Pro Phe Tyr Gly Ala Thr Gly Thr Leu Leu
        35                  40                  45

Leu Phe Val Ala Val Arg Val Leu Glu Ser His Trp Phe Val Trp Ile
    50                  55                  60

Thr Gln Met Asn His Ile Pro Lys Glu Ile Gly His Glu Lys His Arg
65                  70                  75                  80

Asp Trp Ala Ser Ser Gln Leu Ala Ala Thr Cys Asn Val Glu Pro Ser
                85                  90                  95

Leu Phe Ile Asp Trp Phe Ser Gly His Leu Asn Phe Gln Ile Glu His
            100                 105                 110

His Leu Phe Pro Thr Met Thr Arg His Asn Tyr Arg Xaa Val Ala Pro
        115                 120                 125

Leu Val Lys Ala Phe Cys Ala Lys His Gly Leu His Tyr Glu Val
    130                 135                 140
```

(2) INFORMATION FOR SEQ ID NO:12:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:12:

```
CCAAGCTTCT GCAGGAGCTC TTTTTTTTTT TTTTT                                35
```

(2) INFORMATION FOR SEQ ID NO:13:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid -continued (xi) SEQUENCE DESCRIPTION: SEQ ID NO:13:

CUACUACUAC UAGGAGTCCT CTACGGTGTT TTG 33

(2) INFORMATION FOR SEQ ID NO:14:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:14:

CAUCAUCAUC AUATGATGCT CAAGCTGAAA CTG 33

(2) INFORMATION FOR SEQ ID NO:15:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:15:

TACCAACTCG AGAAAATGGC TGCTGCTCCC AGTGTGAGG 39

(2) INFORMATION FOR SEQ ID NO:16:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:16:

AACTGATCTA GATTACTGCG CCTTACCCAT CTTGGAGGC 39

(2) INFORMATION FOR SEQ ID NO:17:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:17:

TACCAACTCG AGAAAATGGC ACCTCCCAAC ACTATCGAT 39

(2) INFORMATION FOR SEQ ID NO:18:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:18:

AACTGATCTA GATTACTTCT TGAAAAAGAC CACGTCTCC 39